(12) United States Patent
Gurskis et al.

(10) Patent No.: US 10,238,446 B2
(45) Date of Patent: Mar. 26, 2019

(54) POSITIONING METHOD AND APPARATUS FOR DELIVERING VAPOR TO THE UTERUS

(71) Applicant: AEGEA MEDICAL INC., Menlo Park, CA (US)

(72) Inventors: Donnell William Gurskis, Belmont, CA (US); Robert Bilgor Peliks, San Francisco, CA (US); Hugh Edward Magen, Belmont, CA (US); Roxanne Daniels, San Francisco, CA (US); Steven Robert Bacich, Half Moon Bay, CA (US)

(73) Assignee: AEGEA MEDICAL INC., Menlo Park, CA (US)

( * ) Notice: Subject to any disclaimer, the term of this patent is extended or adjusted under 35 U.S.C. 154(b) by 0 days.

(21) Appl. No.: 15/689,951

(22) Filed: Aug. 29, 2017

(65) Prior Publication Data

US 2017/0354452 A1    Dec. 14, 2017

Related U.S. Application Data

(63) Continuation of application No. 13/292,889, filed on Nov. 9, 2011, now Pat. No. 9,743,974.
(Continued)

(51) Int. Cl.
*A61B 18/04*    (2006.01)
*A61B 18/00*    (2006.01)

(52) U.S. Cl.
CPC ...... *A61B 18/04* (2013.01); *A61B 2018/0022* (2013.01); *A61B 2018/00559* (2013.01); *A61B 2018/00577* (2013.01)

(58) Field of Classification Search
CPC ............ A61B 18/04; A61B 2018/0022; A61B 2018/00559; A61B 2018/00577
(Continued)

(56) References Cited

U.S. PATENT DOCUMENTS

| 408,899 A | 8/1889 | Small |
| 697,181 A | 4/1902 | Smith |

(Continued)

FOREIGN PATENT DOCUMENTS

| CN | 201189204 Y | 2/2009 |
| CN | 201379631 Y | 1/2010 |

(Continued)

OTHER PUBLICATIONS

Van De Velde; Vapo-cauterization of the uterus; Amer. J. Med. Sci.; vol. CXVIII (118); Nov. 1899.
(Continued)

*Primary Examiner* — Carl H Layno
*Assistant Examiner* — Erin M Piateski
(74) *Attorney, Agent, or Firm* — Shay Glenn LLP

(57) ABSTRACT

A method and system of providing therapy to a patient's uterus. The method can include the steps of inserting a uterine ablation device into the uterus; expanding a distal anchor; inflating a proximal balloon to pull the distal anchor proximally and seat the distal anchor against the internal os of the uterus; inflating a central balloon to seal the cervix; delivering vapor from the uterine ablation device into the uterus; and condensing the vapor on tissue within the uterus. The can include a cervical collar adapted to place a distal portion of the device within the uterus when the cervical collar contacts an external os of the cervix.

5 Claims, 15 Drawing Sheets

Related U.S. Application Data

(60) Provisional application No. 61/411,840, filed on Nov. 9, 2010, provisional application No. 61/544,885, filed on Oct. 7, 2011.

(58) Field of Classification Search
USPC .................................................. 606/28
See application file for complete search history.

(56) References Cited

U.S. PATENT DOCUMENTS

| | | |
|---|---|---|
| 1,719,750 A | 7/1929 | Bridge et al. |
| 3,818,913 A | 6/1974 | Wallach |
| 3,871,374 A | 3/1975 | Bolduc et al. |
| 3,880,168 A | 4/1975 | Berman |
| 3,924,628 A | 12/1975 | Droegemueller et al. |
| 3,930,505 A | 1/1976 | Wallach |
| 4,083,077 A | 4/1978 | Knight et al. |
| 4,447,227 A | 5/1984 | Kotsanis |
| 4,672,962 A | 6/1987 | Hershenson |
| 4,682,596 A | 7/1987 | Bales et al. |
| 4,748,979 A | 6/1988 | Hershenson |
| 4,773,410 A | 9/1988 | Blackmer et al. |
| 4,793,352 A | 12/1988 | Eichenlaub |
| 4,872,920 A | 10/1989 | Flynn et al. |
| 4,898,574 A | 2/1990 | Uchiyama et al. |
| 4,915,113 A | 4/1990 | Holman |
| 4,941,475 A | 7/1990 | Williams et al. |
| 4,950,266 A | 8/1990 | Sinofsky |
| 4,976,711 A | 12/1990 | Parins et al. |
| 4,985,027 A | 1/1991 | Dressel |
| 5,006,119 A | 4/1991 | Acker et al. |
| 5,011,566 A | 4/1991 | Hoffman |
| 5,045,056 A | 9/1991 | Behl |
| 5,078,736 A | 1/1992 | Behl |
| 5,084,043 A | 1/1992 | Hertzmann et al. |
| 5,084,044 A | 1/1992 | Quint |
| 5,102,410 A | 4/1992 | Dressel |
| 5,112,328 A | 5/1992 | Taboada et al. |
| 5,122,138 A | 6/1992 | Manwaring |
| 5,158,536 A | 10/1992 | Sekins et al. |
| 5,162,374 A | 11/1992 | Mulieri et al. |
| 5,190,539 A | 3/1993 | Fletcher et al. |
| 5,217,459 A | 6/1993 | Kamerling |
| 5,217,465 A | 6/1993 | Steppe |
| 5,242,474 A | 9/1993 | Herbst et al. |
| 5,246,436 A | 9/1993 | Rowe |
| 5,263,951 A | 11/1993 | Spears et al. |
| 5,277,201 A | 1/1994 | Stern |
| 5,277,696 A | 1/1994 | Hagen |
| 5,306,274 A | 4/1994 | Long |
| 5,318,014 A | 6/1994 | Carter |
| 5,331,947 A | 7/1994 | Shturman |
| 5,334,190 A | 8/1994 | Seiler |
| 5,344,397 A | 9/1994 | Heaven et al. |
| 5,348,551 A | 9/1994 | Spears et al. |
| 5,352,512 A | 10/1994 | Hoffman |
| 5,417,686 A | 5/1995 | Peterson et al. |
| 5,424,620 A | 6/1995 | Cheon et al. |
| 5,433,708 A | 7/1995 | Nichols et al. |
| 5,433,739 A | 7/1995 | Sluijter et al. |
| 5,437,629 A | 8/1995 | Goldrath |
| 5,443,470 A | 8/1995 | Stern et al. |
| 5,445,168 A | 8/1995 | Krebs |
| 5,449,380 A | 9/1995 | Chin |
| 5,451,208 A | 9/1995 | Goldrath |
| 5,462,521 A | 10/1995 | Brucker et al. |
| 5,500,012 A | 3/1996 | Brucker et al. |
| 5,503,638 A | 4/1996 | Cooper et al. |
| 5,505,730 A | 4/1996 | Edwards |
| 5,524,620 A | 6/1996 | Rosenschein |
| 5,529,076 A | 6/1996 | Schachar |
| 5,540,658 A | 7/1996 | Evans et al. |
| 5,542,928 A | 8/1996 | Evans et al. |
| 5,554,172 A | 9/1996 | Horner et al. |
| 5,562,608 A | 10/1996 | Sekins et al. |
| 5,562,720 A | 10/1996 | Stern et al. |
| 5,584,872 A | 12/1996 | LaFontaine et al. |
| 5,591,157 A | 1/1997 | Hennings et al. |
| 5,616,120 A | 4/1997 | Andrew et al. |
| 5,620,440 A | 4/1997 | Heckele et al. |
| 5,647,871 A | 7/1997 | Levine et al. |
| 5,653,692 A | 8/1997 | Masterson et al. |
| 5,662,671 A | 9/1997 | Barbut et al. |
| 5,665,074 A | 9/1997 | Kelly |
| 5,669,907 A | 9/1997 | Platt et al. |
| 5,674,191 A | 10/1997 | Edwards et al. |
| 5,681,282 A | 10/1997 | Eggers et al. |
| 5,683,366 A | 11/1997 | Eggers et al. |
| 5,688,267 A | 11/1997 | Panescu et al. |
| 5,695,507 A | 12/1997 | Auth et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,707,352 A | 1/1998 | Sekins et al. |
| 5,730,719 A | 3/1998 | Edwards |
| 5,735,811 A | 4/1998 | Brisken |
| 5,741,247 A | 4/1998 | Rizoiu et al. |
| 5,741,248 A | 4/1998 | Stern et al. |
| 5,743,870 A | 4/1998 | Edwards |
| 5,752,965 A | 5/1998 | Francis et al. |
| 5,754,717 A | 5/1998 | Esch |
| 5,755,753 A | 5/1998 | Knowlton |
| 5,769,880 A | 6/1998 | Truckai et al. |
| 5,782,914 A | 7/1998 | Schankereli |
| 5,785,521 A | 7/1998 | Rizoiu et al. |
| 5,800,379 A | 9/1998 | Edwards |
| 5,800,482 A | 9/1998 | Pomeranz et al. |
| 5,800,493 A | 9/1998 | Stevens et al. |
| 5,810,764 A | 9/1998 | Eggers et al. |
| 5,820,580 A | 10/1998 | Edwards et al. |
| 5,824,703 A | 10/1998 | Clark |
| 5,827,268 A | 10/1998 | Laufer |
| 5,836,896 A | 11/1998 | Rosenschein |
| 5,836,906 A | 11/1998 | Edwards |
| 5,843,019 A | 12/1998 | Eggers et al. |
| 5,871,469 A | 2/1999 | Eggers et al. |
| 5,873,855 A | 2/1999 | Eggers et al. |
| 5,879,329 A | 3/1999 | Ginsburg |
| 5,885,243 A | 3/1999 | Capetan et al. |
| 5,888,198 A | 3/1999 | Eggers et al. |
| 5,891,094 A | 4/1999 | Masterson et al. |
| 5,891,095 A | 4/1999 | Eggers et al. |
| 5,891,134 A | 4/1999 | Goble et al. |
| 5,891,457 A | 4/1999 | Neuwirth |
| 5,902,272 A | 5/1999 | Eggers et al. |
| 5,911,734 A | 6/1999 | Tsugita et al. |
| 5,913,856 A | 6/1999 | Chia et al. |
| 5,938,660 A | 8/1999 | Swartz et al. |
| 5,944,686 A | 8/1999 | Patterson et al. |
| 5,944,715 A | 8/1999 | Goble et al. |
| 5,957,919 A | 9/1999 | Laufer |
| 5,964,752 A | 10/1999 | Stone |
| 5,968,037 A | 10/1999 | Rizoiu et al. |
| 5,980,504 A | 11/1999 | Sharkey et al. |
| 5,986,662 A | 11/1999 | Argiro et al. |
| 5,989,212 A | 11/1999 | Sussman et al. |
| 5,989,249 A | 11/1999 | Kirwan |
| 5,989,445 A | 11/1999 | Wise et al. |
| 5,997,499 A | 12/1999 | Sussman et al. |
| 6,004,509 A | 12/1999 | Dey et al. |
| 6,015,406 A | 1/2000 | Goble et al. |
| 6,024,095 A | 2/2000 | Stanley |
| 6,024,733 A | 2/2000 | Eggers et al. |
| 6,027,501 A | 2/2000 | Goble et al. |
| 6,032,077 A | 2/2000 | Pomeranz |
| 6,045,532 A | 4/2000 | Eggers et al. |
| 6,045,549 A | 4/2000 | Smethers et al. |
| 6,047,700 A | 4/2000 | Eggers et al. |
| 6,053,172 A | 4/2000 | Hovda et al. |
| 6,053,909 A | 4/2000 | Shadduck |
| 6,056,746 A | 5/2000 | Goble et al. |
| 6,057,689 A | 5/2000 | Saadat |

(56) References Cited

U.S. PATENT DOCUMENTS

| | | | |
|---|---|---|---|
| 6,059,011 | A | 5/2000 | Giolo |
| 6,063,079 | A | 5/2000 | Hovda et al. |
| 6,063,081 | A | 5/2000 | Mulier et al. |
| 6,066,134 | A | 5/2000 | Eggers et al. |
| 6,066,139 | A | 5/2000 | Ryan et al. |
| 6,080,128 | A | 6/2000 | Sussman et al. |
| 6,080,151 | A | 6/2000 | Swartz et al. |
| 6,083,255 | A | 7/2000 | Laufer et al. |
| 6,086,585 | A | 7/2000 | Hovda et al. |
| 6,095,149 | A | 8/2000 | Sharkey et al. |
| 6,099,251 | A | 8/2000 | LaFleur |
| 6,102,046 | A | 8/2000 | Weinstein et al. |
| 6,102,885 | A | 8/2000 | Bass |
| 6,105,581 | A | 8/2000 | Eggers et al. |
| 6,106,516 | A | 8/2000 | Massengill |
| 6,109,268 | A | 8/2000 | Thapliyal et al. |
| 6,113,597 | A | 9/2000 | Eggers et al. |
| 6,113,722 | A | 9/2000 | Hoffman et al. |
| 6,117,109 | A | 9/2000 | Eggers et al. |
| 6,126,682 | A | 10/2000 | Sharkey et al. |
| 6,130,671 | A | 10/2000 | Argiro |
| 6,139,571 | A | 10/2000 | Fuller et al. |
| 6,149,620 | A | 11/2000 | Baker et al. |
| 6,156,036 | A | 12/2000 | Sussman et al. |
| 6,159,160 | A | 12/2000 | Hsei et al. |
| 6,159,194 | A | 12/2000 | Eggers et al. |
| 6,159,207 | A | 12/2000 | Yoon |
| 6,159,208 | A | 12/2000 | Hovda et al. |
| 6,162,232 | A | 12/2000 | Shadduck |
| 6,174,308 | B1 | 1/2001 | Goble et al. |
| 6,179,805 | B1 | 1/2001 | Sussman et al. |
| 6,179,824 | B1 | 1/2001 | Eggers et al. |
| 6,179,836 | B1 | 1/2001 | Eggers et al. |
| 6,183,469 | B1 | 2/2001 | Thapliyal et al. |
| 6,190,381 | B1 | 2/2001 | Olsen et al. |
| 6,194,066 | B1 | 2/2001 | Hoffman |
| 6,196,989 | B1 | 3/2001 | Padget et al. |
| 6,200,333 | B1 | 3/2001 | Laufer |
| 6,203,542 | B1 | 3/2001 | Ellsberry et al. |
| 6,210,402 | B1 | 4/2001 | Olsen et al. |
| 6,210,404 | B1 | 4/2001 | Shadduck |
| 6,210,405 | B1 | 4/2001 | Goble et al. |
| 6,219,059 | B1 | 4/2001 | Argiro |
| 6,224,592 | B1 | 5/2001 | Eggers et al. |
| 6,228,078 | B1 | 5/2001 | Eggers et al. |
| 6,228,081 | B1 | 5/2001 | Goble |
| 6,228,082 | B1 | 5/2001 | Baker et al. |
| 6,231,567 | B1 | 5/2001 | Rizoiu et al. |
| 6,235,020 | B1 | 5/2001 | Cheng et al. |
| 6,238,391 | B1 | 5/2001 | Olsen et al. |
| 6,254,597 | B1 | 7/2001 | Rizoiu et al. |
| 6,254,600 | B1 | 7/2001 | Willink et al. |
| 6,261,286 | B1 | 7/2001 | Goble et al. |
| 6,261,311 | B1 | 7/2001 | Sharkey et al. |
| 6,264,650 | B1 | 7/2001 | Hovda et al. |
| 6,264,651 | B1 | 7/2001 | Underwood et al. |
| 6,264,652 | B1 | 7/2001 | Eggers et al. |
| 6,277,112 | B1 | 8/2001 | Underwood et al. |
| 6,277,114 | B1 | 8/2001 | Bullivant et al. |
| 6,283,910 | B1 | 9/2001 | Bradshaw et al. |
| 6,283,961 | B1 | 9/2001 | Underwood et al. |
| 6,283,989 | B1 | 9/2001 | Laufer et al. |
| 6,290,715 | B1 | 9/2001 | Sharkey et al. |
| 6,293,942 | B1 | 9/2001 | Goble et al. |
| 6,296,636 | B1 | 10/2001 | Cheng et al. |
| 6,296,638 | B1 | 10/2001 | Davison et al. |
| 6,299,633 | B1 | 10/2001 | Laufer |
| 6,300,150 | B1 | 10/2001 | Venkatasubramanian |
| 6,306,129 | B1 | 10/2001 | Little et al. |
| 6,306,134 | B1 | 10/2001 | Goble et al. |
| 6,309,387 | B1 | 10/2001 | Eggers et al. |
| 6,312,408 | B1 | 11/2001 | Eggers et al. |
| 6,312,474 | B1 | 11/2001 | Francis et al. |
| 6,315,755 | B1 | 11/2001 | Sussman |
| 6,319,221 | B1 | 11/2001 | Savage et al. |
| 6,322,549 | B1 | 11/2001 | Eggers et al. |
| 6,327,505 | B1 | 12/2001 | Medhkour et al. |
| 6,331,171 | B1 | 12/2001 | Cohen |
| 6,355,032 | B1 | 3/2002 | Hovda et al. |
| 6,361,531 | B1 | 3/2002 | Hissong |
| 6,363,937 | B1 | 4/2002 | Hovda et al. |
| 6,364,877 | B1 | 4/2002 | Goble et al. |
| 6,375,635 | B1 | 4/2002 | Moutafis et al. |
| 6,379,350 | B1 | 4/2002 | Sharkey et al. |
| 6,379,351 | B1 | 4/2002 | Thapliyal et al. |
| 6,391,025 | B1 | 5/2002 | Weinstein et al. |
| 6,394,949 | B1 | 5/2002 | Crowley et al. |
| 6,394,996 | B1 | 5/2002 | Lawrence et al. |
| 6,398,759 | B1 | 6/2002 | Sussman et al. |
| 6,398,775 | B1 | 6/2002 | Perkins et al. |
| 6,409,699 | B1 | 6/2002 | Ash |
| 6,409,723 | B1 | 6/2002 | Edwards |
| 6,416,507 | B1 | 7/2002 | Eggers et al. |
| 6,416,508 | B1 | 7/2002 | Eggers et al. |
| 6,416,509 | B1 | 7/2002 | Goble et al. |
| 6,432,103 | B1 | 8/2002 | Ellsberry et al. |
| 6,440,089 | B1 | 8/2002 | Shine |
| 6,458,231 | B1 | 10/2002 | Wapner et al. |
| 6,461,350 | B1 | 10/2002 | Underwood et al. |
| 6,461,354 | B1 | 10/2002 | Olsen et al. |
| 6,464,694 | B1 | 10/2002 | Massengill |
| 6,464,695 | B2 | 10/2002 | Hovda et al. |
| 6,468,270 | B1 | 10/2002 | Hovda et al. |
| 6,468,274 | B1 | 10/2002 | Alleyne et al. |
| 6,468,313 | B1 | 10/2002 | Claeson et al. |
| 6,475,215 | B1 | 11/2002 | Tanrisever |
| 6,482,201 | B1 | 11/2002 | Olsen et al. |
| 6,488,673 | B1 | 12/2002 | Laufer et al. |
| 6,493,589 | B1 | 12/2002 | Medhkour et al. |
| 6,500,173 | B2 | 12/2002 | Underwood et al. |
| 6,508,816 | B2 | 1/2003 | Shadduck |
| 6,510,854 | B2 | 1/2003 | Goble |
| 6,517,533 | B1 | 2/2003 | Swaminathan |
| 6,522,930 | B1 | 2/2003 | Schaer et al. |
| 6,527,761 | B1 | 3/2003 | Soltesz et al. |
| 6,527,766 | B1 | 3/2003 | Bair |
| 6,540,741 | B1 | 4/2003 | Underwood et al. |
| 6,544,211 | B1 | 4/2003 | Andrew et al. |
| 6,544,261 | B2 | 4/2003 | Ellsberry et al. |
| 6,547,784 | B1 | 4/2003 | Thompson et al. |
| 6,551,271 | B2 | 4/2003 | Nguyen |
| 6,551,274 | B2 | 4/2003 | Heiner |
| 6,554,780 | B1 | 4/2003 | Sampson et al. |
| 6,557,559 | B1 | 5/2003 | Eggers et al. |
| 6,558,379 | B1 | 5/2003 | Batchelor et al. |
| 6,565,561 | B1 * | 5/2003 | Goble ................ A61B 18/148 606/41 |
| 6,569,146 | B1 | 5/2003 | Werner et al. |
| 6,575,929 | B2 | 6/2003 | Sussman et al. |
| 6,575,933 | B1 | 6/2003 | Wittenberger et al. |
| 6,575,968 | B1 | 6/2003 | Eggers et al. |
| 6,579,270 | B2 | 6/2003 | Sussman et al. |
| 6,582,423 | B1 | 6/2003 | Thapliyal et al. |
| 6,585,639 | B1 | 7/2003 | Kotmel et al. |
| 6,588,613 | B1 | 7/2003 | Pechenik et al. |
| 6,589,201 | B1 | 7/2003 | Sussman et al. |
| 6,589,237 | B2 | 7/2003 | Woloszko et al. |
| 6,592,594 | B2 | 7/2003 | Rimbaugh et al. |
| 6,595,990 | B1 | 7/2003 | Weinstein et al. |
| 6,599,311 | B1 | 7/2003 | Biggs et al. |
| 6,602,248 | B1 | 8/2003 | Sharps et al. |
| 6,610,043 | B1 | 8/2003 | Ingenito |
| 6,620,155 | B2 | 9/2003 | Underwood et al. |
| 6,623,444 | B2 | 9/2003 | Babaev |
| 6,626,855 | B1 | 9/2003 | Weng et al. |
| 6,629,974 | B2 | 10/2003 | Penny et al. |
| 6,632,193 | B1 | 10/2003 | Davison et al. |
| 6,632,220 | B1 | 10/2003 | Eggers et al. |
| 6,634,363 | B1 | 10/2003 | Danek et al. |
| 6,653,525 | B2 | 11/2003 | Ingenito et al. |
| 6,669,685 | B1 | 12/2003 | Rizoiu et al. |
| 6,669,694 | B2 | 12/2003 | Shadduck |
| 6,676,628 | B2 | 1/2004 | Sussman et al. |
| 6,676,629 | B2 | 1/2004 | Andrew et al. |

(56) References Cited

U.S. PATENT DOCUMENTS

| | | |
|---|---|---|
| 6,679,264 B1 | 1/2004 | Deem et al. |
| 6,679,879 B2 | 1/2004 | Shadduck |
| 6,692,494 B1 | 2/2004 | Cooper et al. |
| 6,695,839 B2 | 2/2004 | Sharkey et al. |
| 6,699,212 B1 | 3/2004 | Kadziauskas et al. |
| 6,699,244 B2 | 3/2004 | Carranza et al. |
| 6,708,056 B2 | 3/2004 | Duchon et al. |
| 6,712,811 B2 | 3/2004 | Underwood et al. |
| 6,712,812 B2 | 3/2004 | Roschak et al. |
| 6,719,754 B2 | 4/2004 | Underwood et al. |
| 6,726,684 B1 | 4/2004 | Woloszko et al. |
| 6,726,708 B2 | 4/2004 | Lasheras |
| 6,746,447 B2 | 6/2004 | Davison et al. |
| 6,749,604 B1 | 6/2004 | Eggers et al. |
| 6,755,794 B2 | 6/2004 | Soukup |
| 6,758,846 B2 | 7/2004 | Goble et al. |
| 6,763,836 B2 | 7/2004 | Tasto et al. |
| 6,766,202 B2 | 7/2004 | Underwood et al. |
| 6,770,070 B1 | 8/2004 | Balbierz |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,776,765 B2 | 8/2004 | Soukup et al. |
| 6,780,180 B1 | 8/2004 | Goble et al. |
| 6,805,130 B2 | 10/2004 | Tasto et al. |
| 6,813,520 B2 | 11/2004 | Truckai et al. |
| 6,832,996 B2 | 12/2004 | Woloszko et al. |
| 6,837,884 B2 | 1/2005 | Woloszko |
| 6,837,887 B2 | 1/2005 | Woloszko et al. |
| 6,837,888 B2 | 1/2005 | Ciarrocca et al. |
| 6,852,108 B2 | 2/2005 | Barry et al. |
| 6,860,847 B2 | 3/2005 | Alferness et al. |
| 6,875,194 B2 | 4/2005 | MacKool |
| 6,896,672 B1 | 5/2005 | Eggers et al. |
| 6,896,674 B1 | 5/2005 | Woloszko et al. |
| 6,896,675 B2 | 5/2005 | Leung et al. |
| 6,896,690 B1 | 5/2005 | Lambrecht et al. |
| 6,901,927 B2 | 6/2005 | Deem et al. |
| 6,904,909 B2 | 6/2005 | Andreas et al. |
| 6,907,881 B2 | 6/2005 | Suki et al. |
| 6,911,028 B2 | 6/2005 | Shadduck |
| 6,915,806 B2 | 7/2005 | Pacek et al. |
| 6,918,903 B2 | 7/2005 | Bass |
| 6,921,385 B2 | 7/2005 | Clements et al. |
| 6,929,640 B1 | 8/2005 | Underwood et al. |
| 6,929,642 B2 | 8/2005 | Xiao et al. |
| 6,949,096 B2 | 9/2005 | Davison et al. |
| 6,955,675 B2 | 10/2005 | Jain |
| 6,960,204 B2 | 11/2005 | Eggers et al. |
| 6,962,584 B1 | 11/2005 | Stone et al. |
| 6,972,014 B2 | 12/2005 | Eum et al. |
| 6,978,174 B2 | 12/2005 | Gelfand et al. |
| 6,986,769 B2 | 1/2006 | Nelson et al. |
| 6,991,028 B2 | 1/2006 | Comeaux et al. |
| 6,991,631 B2 | 1/2006 | Woloszko et al. |
| 7,004,940 B2 | 2/2006 | Ryan et al. |
| 7,004,941 B2 | 2/2006 | Tvinnereim et al. |
| 7,022,688 B1 | 4/2006 | Keast et al. |
| 7,031,504 B1 | 4/2006 | Argiro et al. |
| 7,070,596 B1 | 7/2006 | Woloszko et al. |
| 7,083,612 B2 | 8/2006 | Littrup et al. |
| 7,094,215 B2 | 8/2006 | Davison et al. |
| 7,094,249 B1 | 8/2006 | Broome et al. |
| 7,101,367 B2 | 9/2006 | Xiao et al. |
| 7,104,986 B2 | 9/2006 | Hovda et al. |
| 7,105,007 B2 | 9/2006 | Hibler |
| RE39,358 E | 10/2006 | Goble |
| 7,128,748 B2 | 10/2006 | Mooradian et al. |
| 7,131,969 B1 | 11/2006 | Hovda et al. |
| 7,136,064 B2 | 11/2006 | Zuiderveld |
| 7,144,402 B2 | 12/2006 | Kuester |
| 7,144,588 B2 | 12/2006 | Oray et al. |
| 7,162,303 B2 | 1/2007 | Levin et al. |
| 7,169,143 B2 | 1/2007 | Eggers et al. |
| 7,179,255 B2 | 2/2007 | Lettice et al. |
| 7,186,234 B2 | 3/2007 | Dahla et al. |
| 7,192,400 B2 | 3/2007 | Campbell et al. |
| 7,192,428 B2 | 3/2007 | Eggers et al. |
| 7,201,750 B1 | 4/2007 | Eggers et al. |
| 7,217,268 B2 | 5/2007 | Eggers et al. |
| 7,233,820 B2 | 6/2007 | Gilboa |
| 7,235,070 B2 | 6/2007 | Vanney |
| 7,241,293 B2 | 7/2007 | Davison |
| 7,270,658 B2 | 9/2007 | Woloszko et al. |
| 7,270,659 B2 | 9/2007 | Ricart et al. |
| 7,270,661 B2 | 9/2007 | Dahla et al. |
| 7,276,063 B2 | 10/2007 | Davison et al. |
| 7,297,143 B2 | 11/2007 | Woloszko et al. |
| 7,297,145 B2 | 11/2007 | Woloszko et al. |
| 7,311,708 B2 | 12/2007 | McClurken |
| 7,320,325 B2 | 1/2008 | Duchon et al. |
| 7,335,195 B2 | 2/2008 | Mehier |
| 7,347,859 B2 | 3/2008 | Garabedian et al. |
| 7,524,315 B2 | 4/2009 | Blott et al. |
| 7,585,295 B2 | 9/2009 | Ben-Nun |
| 7,617,005 B2 | 11/2009 | Demarais et al. |
| 7,620,451 B2 | 11/2009 | Demarais et al. |
| 7,653,438 B2 | 1/2010 | Deem et al. |
| 7,756,583 B2 | 7/2010 | Demarais et al. |
| 7,815,616 B2 | 10/2010 | Boehringer et al. |
| 7,815,646 B2 | 10/2010 | Hart |
| 7,853,333 B2 | 12/2010 | Demarais |
| 7,873,417 B2 | 1/2011 | Demarais et al. |
| 7,937,143 B2 | 5/2011 | Demarais et al. |
| 7,993,323 B2 | 8/2011 | Barry et al. |
| 8,131,371 B2 | 3/2012 | Demarals et al. |
| 8,145,316 B2 | 3/2012 | Deem et al. |
| 8,145,317 B2 | 3/2012 | Demarais et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,192,424 B2 | 6/2012 | Woloszko |
| 8,197,470 B2 | 6/2012 | Sharkey et al. |
| 8,216,217 B2 | 7/2012 | Sharkey et al. |
| 8,221,401 B2 | 7/2012 | Sharkey et al. |
| 8,221,403 B2 | 7/2012 | Sharkey et al. |
| 8,313,485 B2 | 11/2012 | Shadduck |
| 8,574,226 B2 | 11/2013 | Shadduck |
| 8,579,888 B2 | 11/2013 | Hoey et al. |
| 8,579,892 B2 | 11/2013 | Hoey et al. |
| 8,585,645 B2 | 11/2013 | Barry et al. |
| 8,585,692 B2 | 11/2013 | Shadduck et al. |
| 8,801,702 B2 | 8/2014 | Hoey et al. |
| 8,900,223 B2 | 12/2014 | Shadduck |
| 9,662,060 B2 | 5/2017 | Peliks et al. |
| 9,743,974 B2 | 8/2017 | Gurskis et al. |
| 9,907,599 B2 | 3/2018 | Hoey et al. |
| 2002/0007180 A1 | 1/2002 | Wittenberger et al. |
| 2002/0013601 A1 | 1/2002 | Nobles et al. |
| 2002/0019627 A1 | 2/2002 | Maguire et al. |
| 2002/0077516 A1 | 6/2002 | Flanigan |
| 2002/0078956 A1 | 6/2002 | Sharpe et al. |
| 2002/0111386 A1 | 8/2002 | Sekins et al. |
| 2002/0128638 A1 | 9/2002 | Chauvet et al. |
| 2002/0133147 A1 | 9/2002 | Marchitto et al. |
| 2002/0151917 A1 | 10/2002 | Barry |
| 2002/0161326 A1 | 10/2002 | Sussman et al. |
| 2002/0173815 A1 | 11/2002 | Hogendijk et al. |
| 2002/0177846 A1 | 11/2002 | Mulier et al. |
| 2003/0028189 A1 | 2/2003 | Woloszko et al. |
| 2003/0097126 A1 | 5/2003 | Woloszko et al. |
| 2003/0099279 A1 | 5/2003 | Venkatasubramanian et al. |
| 2003/0130738 A1 | 7/2003 | Hovda et al. |
| 2003/0144654 A1 | 7/2003 | Hilal |
| 2003/0158545 A1 | 8/2003 | Hovda et al. |
| 2003/0163178 A1 | 8/2003 | Davison et al. |
| 2003/0181922 A1 | 9/2003 | Alferness |
| 2003/0212394 A1 | 11/2003 | Pearson et al. |
| 2003/0217962 A1 | 11/2003 | Childers et al. |
| 2003/0220604 A1 | 11/2003 | Al-Anazi |
| 2003/0225364 A1 | 12/2003 | Kraft et al. |
| 2004/0002698 A1 | 1/2004 | Hua Xiao et al. |
| 2004/0024399 A1 | 2/2004 | Sharps et al. |
| 2004/0047855 A1 | 3/2004 | Ingenito |

(56) References Cited

U.S. PATENT DOCUMENTS

| | | |
|---|---|---|
| 2004/0049180 A1 | 3/2004 | Sharps et al. |
| 2004/0055606 A1 | 3/2004 | Hendricksen et al. |
| 2004/0068306 A1 | 4/2004 | Shadduck |
| 2004/0116922 A1 | 6/2004 | Hovda et al. |
| 2004/0199226 A1 | 10/2004 | Shadduck |
| 2004/0230190 A1 | 11/2004 | Dahla et al. |
| 2005/0010205 A1 | 1/2005 | Hovda et al. |
| 2005/0119650 A1 | 6/2005 | Sanders et al. |
| 2005/0143728 A1 | 6/2005 | Sampson et al. |
| 2005/0166925 A1 | 8/2005 | Wilson et al. |
| 2005/0171574 A1 | 8/2005 | Rubinsky et al. |
| 2005/0171582 A1 | 8/2005 | Matlock |
| 2005/0177147 A1 | 8/2005 | Vancelette et al. |
| 2005/0215991 A1 | 9/2005 | Altman et al. |
| 2005/0222485 A1 | 10/2005 | Shaw et al. |
| 2005/0228423 A1 | 10/2005 | Khashayar et al. |
| 2005/0228424 A1 | 10/2005 | Khashayar et al. |
| 2005/0240171 A1 | 10/2005 | Forrest |
| 2005/0267467 A1 | 12/2005 | Paul et al. |
| 2005/0283143 A1 | 12/2005 | Rizoiu |
| 2006/0004400 A1 | 1/2006 | McGurk et al. |
| 2006/0047291 A1 | 3/2006 | Barry |
| 2006/0058831 A1* | 3/2006 | Atad .............. A61M 25/1002 606/193 |
| 2006/0085054 A1 | 4/2006 | Zikorus et al. |
| 2006/0100619 A1 | 5/2006 | McClurken et al. |
| 2006/0130830 A1 | 6/2006 | Barry |
| 2006/0135955 A1 | 6/2006 | Shadduck |
| 2006/0142783 A1 | 6/2006 | Lewis et al. |
| 2006/0161233 A1 | 7/2006 | Barry et al. |
| 2006/0200076 A1 | 9/2006 | Gonzalez et al. |
| 2006/0206150 A1 | 9/2006 | Demarais et al. |
| 2006/0224154 A1 | 10/2006 | Shadduck et al. |
| 2006/0265053 A1 | 11/2006 | Hunt |
| 2006/0271111 A1 | 11/2006 | Demarais et al. |
| 2007/0021713 A1 | 1/2007 | Kumar et al. |
| 2007/0032785 A1 | 2/2007 | Diederich et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0225744 A1 | 9/2007 | Nobles et al. |
| 2007/0239197 A1 | 10/2007 | Dubey et al. |
| 2007/0288051 A1 | 12/2007 | Beyer et al. |
| 2008/0033493 A1 | 2/2008 | Deckman et al. |
| 2008/0077201 A1 | 3/2008 | Levinson et al. |
| 2008/0125747 A1 | 5/2008 | Prokop |
| 2008/0132826 A1 | 6/2008 | Shadduck et al. |
| 2008/0135053 A1 | 6/2008 | Gruber et al. |
| 2008/0161788 A1 | 7/2008 | Dando et al. |
| 2008/0167664 A1 | 7/2008 | Payne et al. |
| 2008/0249467 A1 | 10/2008 | Burnett et al. |
| 2009/0024108 A1 | 1/2009 | Lee-Sepsick et al. |
| 2009/0030412 A1 | 1/2009 | Willis et al. |
| 2009/0054871 A1* | 2/2009 | Sharkey .............. A61B 18/04 604/515 |
| 2009/0076409 A1 | 3/2009 | Wu et al. |
| 2009/0125010 A1 | 5/2009 | Sharkey et al. |
| 2009/0216220 A1 | 8/2009 | Hoey et al. |
| 2009/0306640 A1 | 12/2009 | Glaze et al. |
| 2010/0078046 A1 | 4/2010 | Labib et al. |
| 2010/0082021 A1 | 4/2010 | Gutierrez et al. |
| 2010/0094270 A1* | 4/2010 | Sharma .............. A61B 18/04 606/27 |
| 2010/0100091 A1 | 4/2010 | Truckai |
| 2010/0100094 A1 | 4/2010 | Truckai |
| 2010/0106152 A1 | 4/2010 | Truckai et al. |
| 2010/0114083 A1 | 5/2010 | Sharma |
| 2010/0114089 A1 | 5/2010 | Truckai et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0179528 A1 | 7/2010 | Shadduck et al. |
| 2010/0204688 A1* | 8/2010 | Hoey .............. A61B 18/04 606/27 |
| 2010/0228222 A1 | 9/2010 | Williams et al. |
| 2010/0249773 A1 | 9/2010 | Clark et al. |
| 2010/0262133 A1 | 10/2010 | Hoey et al. |
| 2011/0009829 A1 | 1/2011 | Kosinski et al. |
| 2011/0054508 A1 | 3/2011 | Zhou et al. |
| 2011/0077628 A1 | 3/2011 | Hoey et al. |
| 2011/0112400 A1 | 5/2011 | Emery et al. |
| 2011/0112432 A1 | 5/2011 | Toth |
| 2011/0112433 A1 | 5/2011 | Toth |
| 2011/0112523 A1 | 5/2011 | Toth et al. |
| 2011/0118718 A1 | 5/2011 | Toth et al. |
| 2011/0118719 A1 | 5/2011 | Vissy et al. |
| 2011/0160648 A1 | 6/2011 | Hoey |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0208096 A1 | 8/2011 | Demarais et al. |
| 2011/0208178 A1 | 8/2011 | Truckai |
| 2011/0257564 A1 | 10/2011 | Demarais et al. |
| 2011/0264011 A1 | 10/2011 | Wu et al. |
| 2011/0264075 A1 | 10/2011 | Leung et al. |
| 2011/0264090 A1 | 10/2011 | Shadduck et al. |
| 2012/0065632 A1 | 3/2012 | Shadduck |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0116383 A1 | 5/2012 | Mauch et al. |
| 2012/0116486 A1 | 5/2012 | Naga et al. |
| 2012/0130359 A1 | 5/2012 | Turovskiy |
| 2012/0130360 A1 | 5/2012 | Buckley et al. |
| 2012/0130458 A1 | 5/2012 | Ryba et al. |
| 2012/0136343 A1 | 5/2012 | Burnett |
| 2012/0136344 A1 | 5/2012 | Buckley et al. |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143293 A1 | 6/2012 | Mauch et al. |
| 2012/0150267 A1 | 6/2012 | Buckley et al. |
| 2012/0158104 A1 | 6/2012 | Huynh et al. |
| 2012/0197198 A1 | 8/2012 | Demarais et al. |
| 2012/0197245 A1 | 8/2012 | Burnett et al. |
| 2012/0209281 A1 | 8/2012 | Truckai |
| 2012/0232545 A1 | 9/2012 | Truckai et al. |
| 2012/0245583 A1 | 9/2012 | Truckai et al. |
| 2012/0259271 A1 | 10/2012 | Shadduck et al. |
| 2012/0283717 A1 | 11/2012 | Sharkey et al. |
| 2013/0006231 A1 | 1/2013 | Sharma et al. |
| 2013/0116683 A1 | 5/2013 | Shadduck et al. |
| 2013/0237978 A1 | 9/2013 | Shadduck et al. |
| 2013/0296837 A1 | 11/2013 | Burnett et al. |
| 2014/0200570 A1 | 7/2014 | Hoey et al. |
| 2015/0335373 A1 | 11/2015 | Chee et al. |
| 2015/0335380 A1 | 11/2015 | Chee et al. |
| 2017/0258511 A1 | 9/2017 | Peliks et al. |
| 2018/0199982 A1 | 7/2018 | Hoey et al. |
| 2018/0289416 A1 | 10/2018 | Chee et al. |

FOREIGN PATENT DOCUMENTS

| | | |
|---|---|---|
| CN | 102271602 A | 12/2011 |
| EP | 2198797 A1 | 6/2012 |
| JP | H06-285074 A | 10/1994 |
| JP | 2000502585 A | 3/2000 |
| JP | 20003513742 A | 4/2003 |
| JP | 2010516351 A | 5/2010 |
| WO | WO99/53853 A1 | 10/1999 |
| WO | WO00/011927 A2 | 3/2000 |
| WO | WO00/29055 A1 | 5/2000 |
| WO | WO01/85012 A2 | 11/2001 |
| WO | WO02/069821 A1 | 9/2002 |
| WO | WO 03/070302 A1 | 8/2003 |
| WO | WO2005/025635 A2 | 3/2005 |
| WO | WO2005/102175 A2 | 11/2005 |
| WO | WO2006/003665 A2 | 1/2006 |
| WO | WO 2006/055695 A1 | 5/2006 |
| WO | WO06/108974 A1 | 10/2006 |
| WO | WO2009/009398 A1 | 1/2009 |
| WO | WO2010/045055 A2 | 4/2010 |
| WO | WO2010/048007 A1 | 4/2010 |

(56) References Cited

FOREIGN PATENT DOCUMENTS

| WO | WO2011/025658 A1 | 3/2011 |
|---|---|---|
| WO | WO2011/053599 A1 | 5/2011 |
| WO | WO2011/060189 A1 | 5/2011 |
| WO | WO2011/060191 A1 | 5/2011 |
| WO | WO2012/106260 A2 | 8/2012 |

OTHER PUBLICATIONS

Blacker; Vaporization of the uterus; J. Obstet. & Gyn.; vol. 1; Issue 5; pp. 488-511; May 1902.

Neuwirth et al.; The endometrial ablator: a new instrument; Obst. & Gyn.; vol. 83; No. 5; part 1; pp. 792-796; May 1994.

Prior et al.; Treatment of mennorrhagia by radiofrequency heating; Int. J. Hyperthermia; vol. 7; No. 2; pp. 213-220; Mar.-Apr. 1991.

Baker et al.; Threshold intrauterine perfusion pressures for intraperitoneal spill during hydrotubation and correlation with tubal adhesive diseases; Fertility and Sterility; 64(6); pp. 1066-1069; Dec. 31, 1995.

Fishman et. al.; A randomized trial comparing lung-volume-reduction surgery with medical therapy for severe emphysema; N Engl J Med; 348(210. pp. 2059-2073; May 22, 2003.

Homasson et. al.; Bronchoscopic cryotherapy for airway strictures caused by tumors; Chest; 90(2); pp. 159-164; Aug. 1, 1986.

Marasso et al.; Radiofrequency resection of bronchial tumours in combination with cryotherapy: evaluation of a new technique; Thorax; 53(2); pp. 106-109; Feb. 1998.

Marasso et. al.; Cryosurgery in bronchoscopic treatment of tracheobronchial stenosis; Cheat; 103(2); pp. 472-474; Feb. 1993.

Morice et. al; Endobronchial argon plasma coagulation for treatment of hemoptysis and neoplastic airway obstruction; Chest; 119(3); pp. 781-787; Mar. 1, 2001.

Tschirren et. al.; Intrathoracic airway trees: segmentation and airway morphology analysis from low-dose CT scans; IEEE Transactions on Medical Imaging; 24(12); pp. 1529-1539; Dec. 2005.

Unger et. al.; Monolithic Microfabricated Valves and Pumps by Multilayer Soft Lithography; Science, 288(5463); pp. 113-116; Apr. 7, 2000.

* cited by examiner

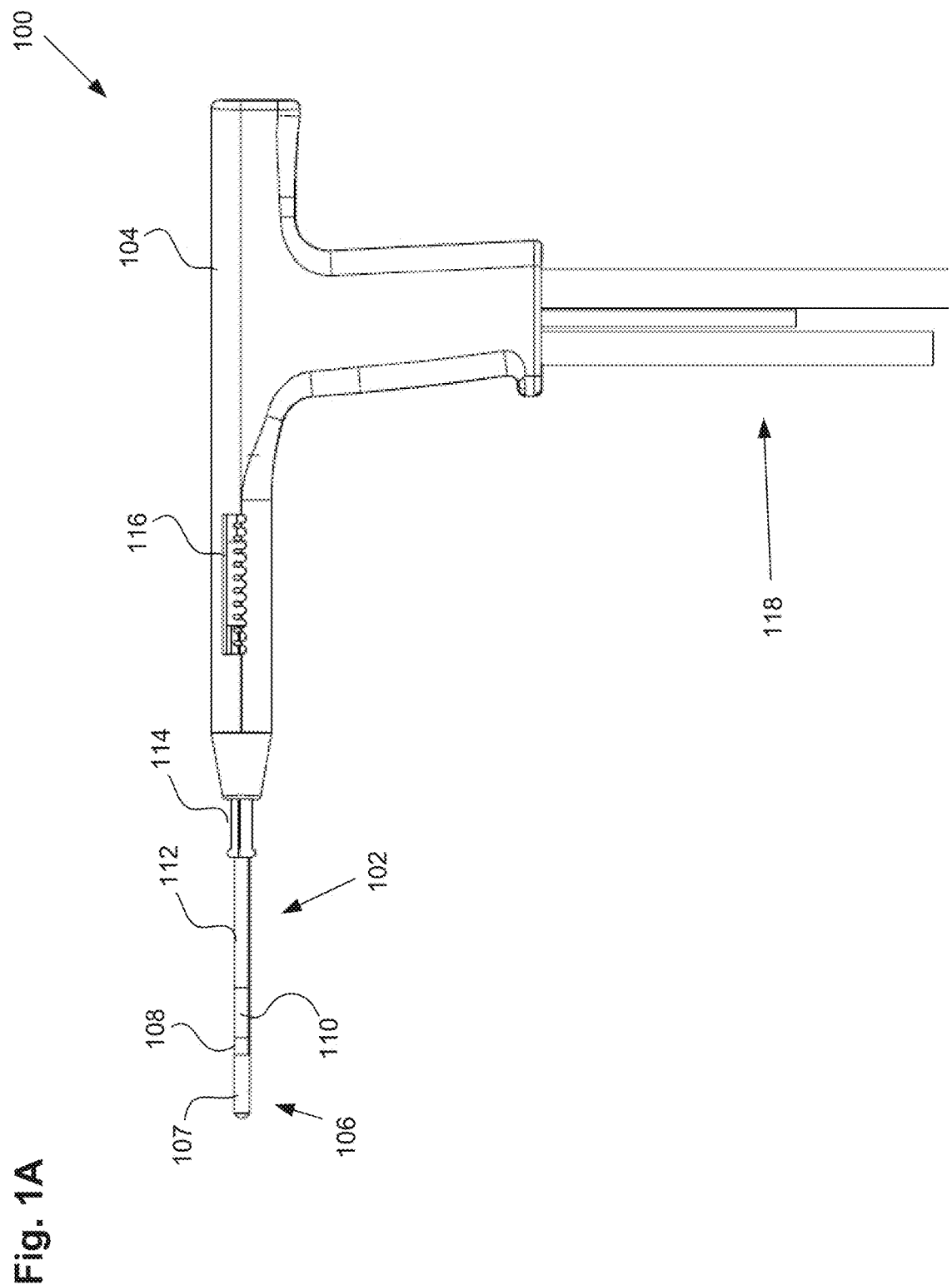

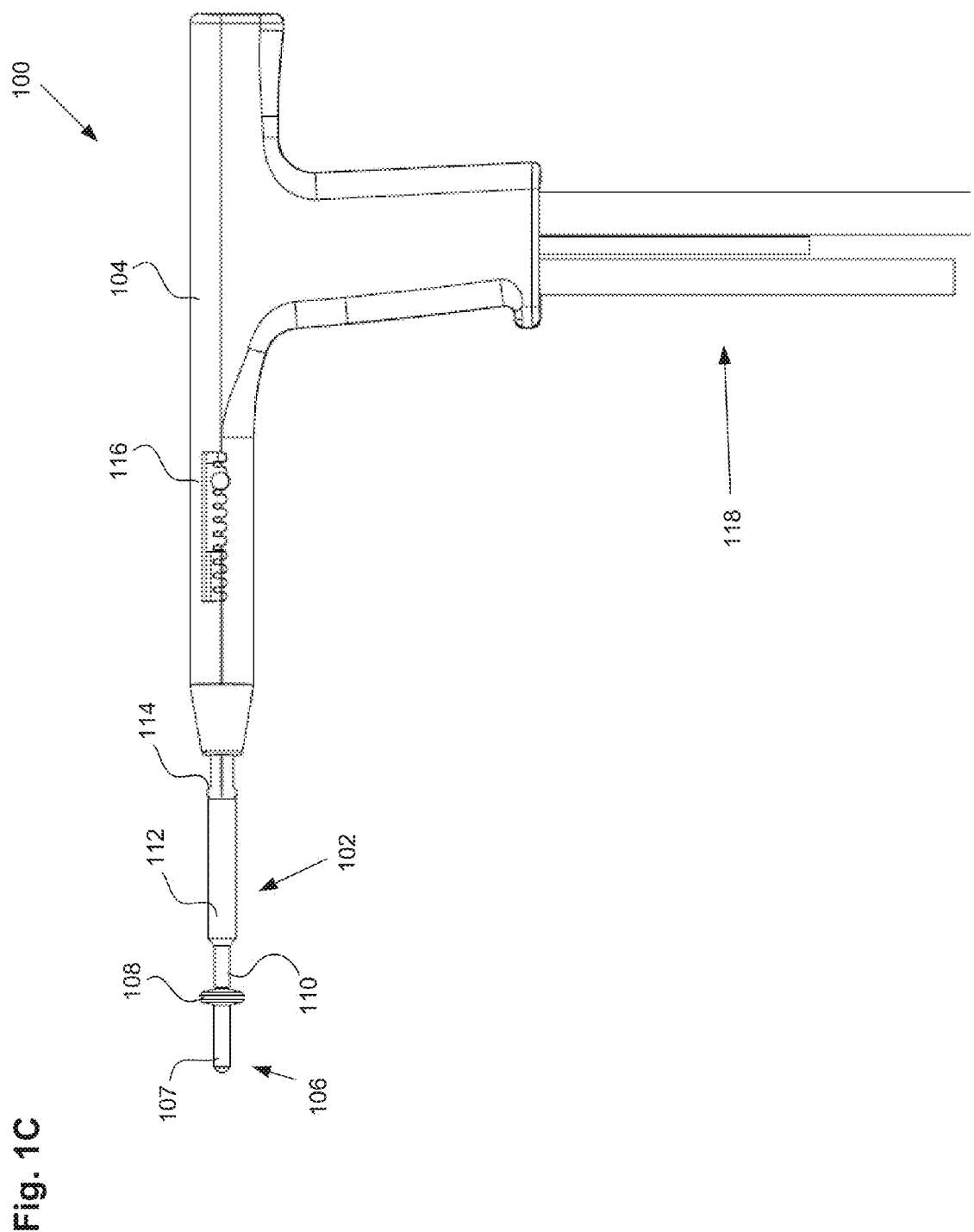

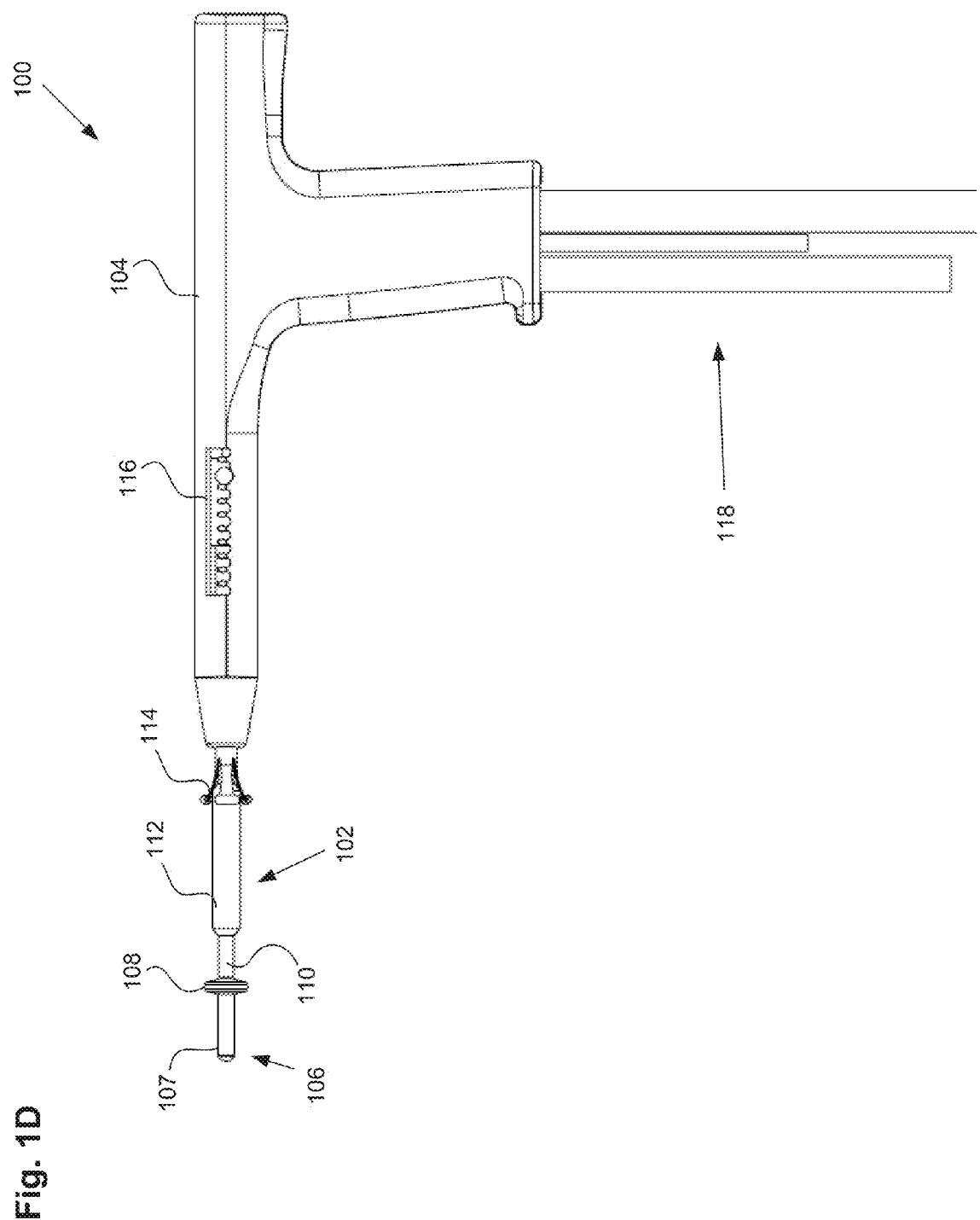

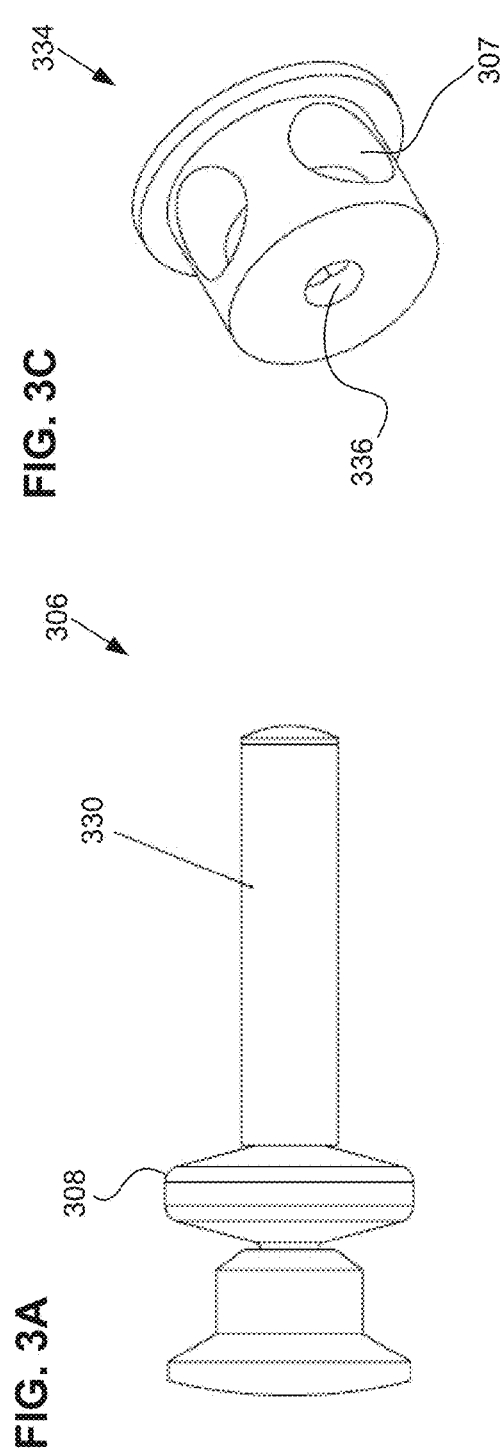
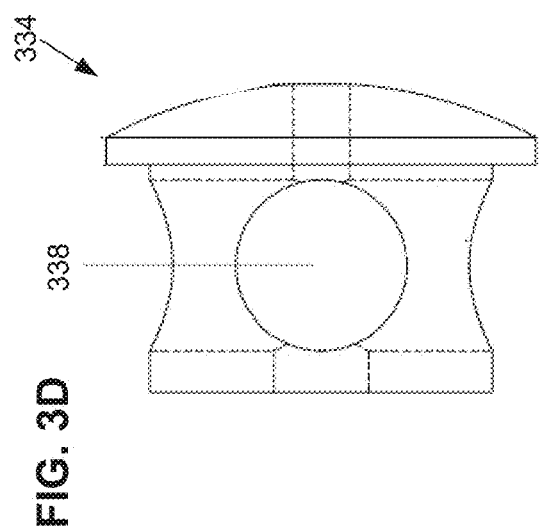
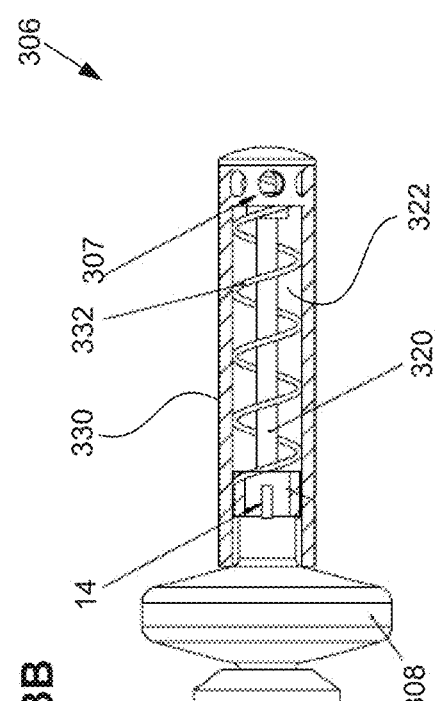

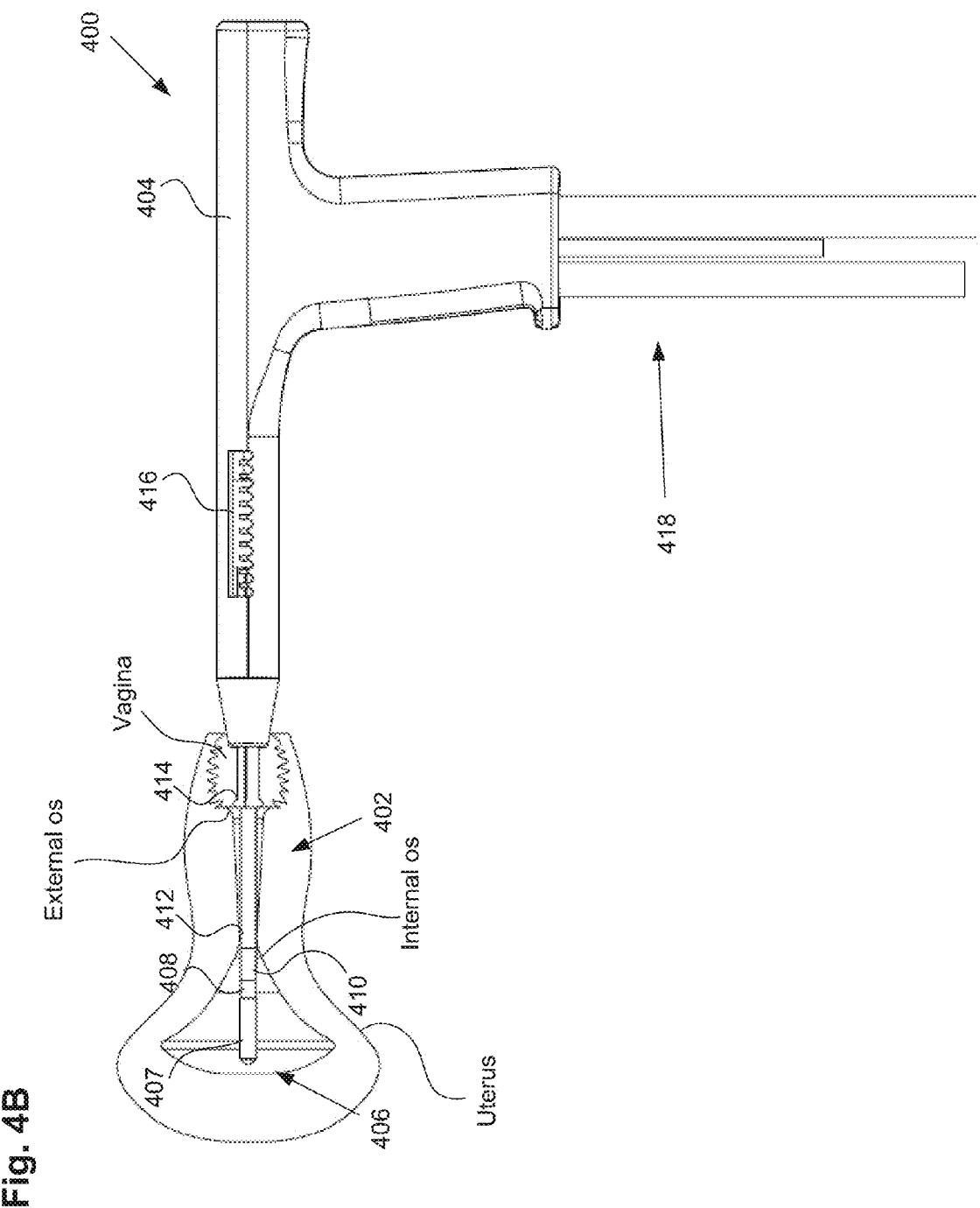

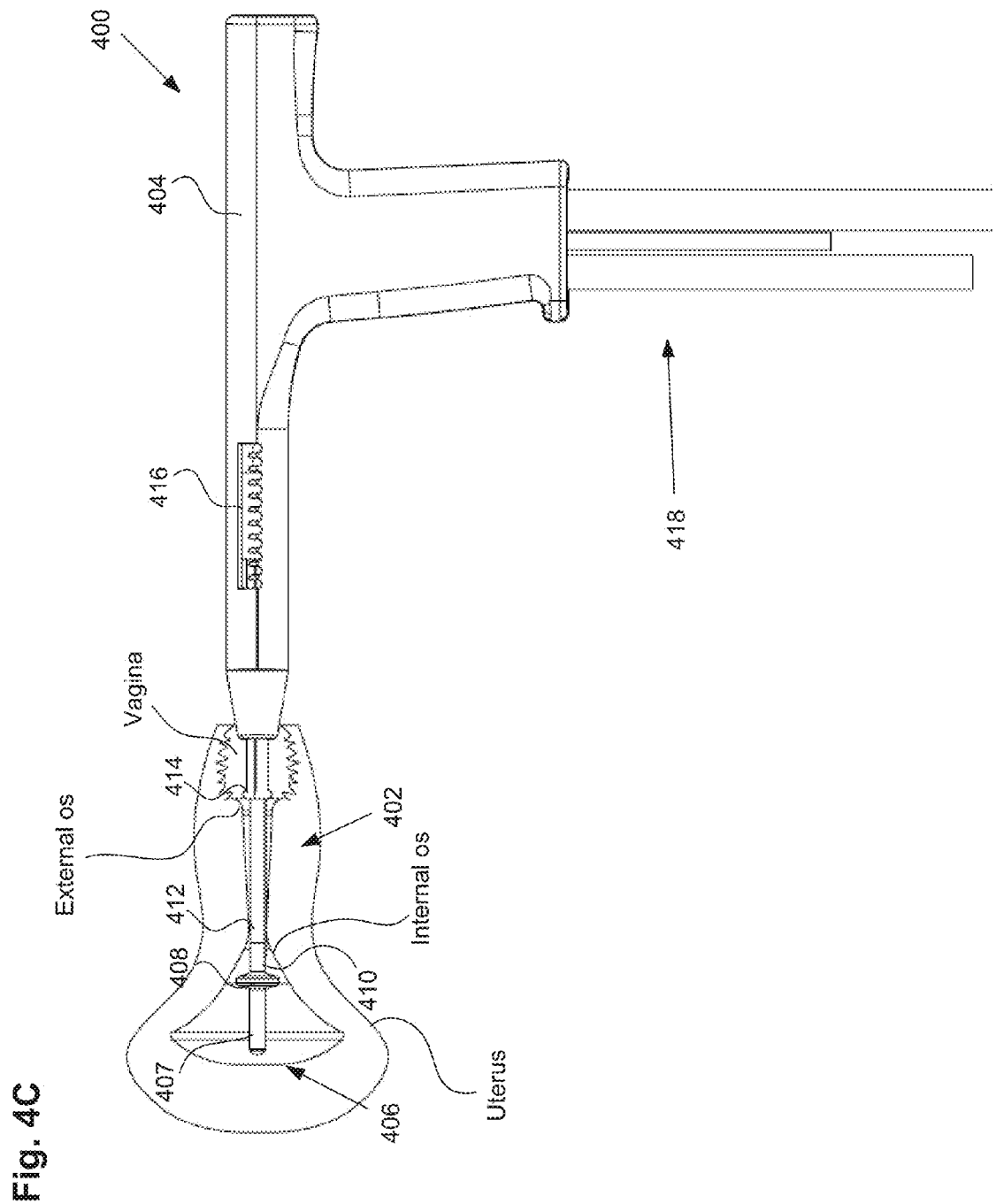

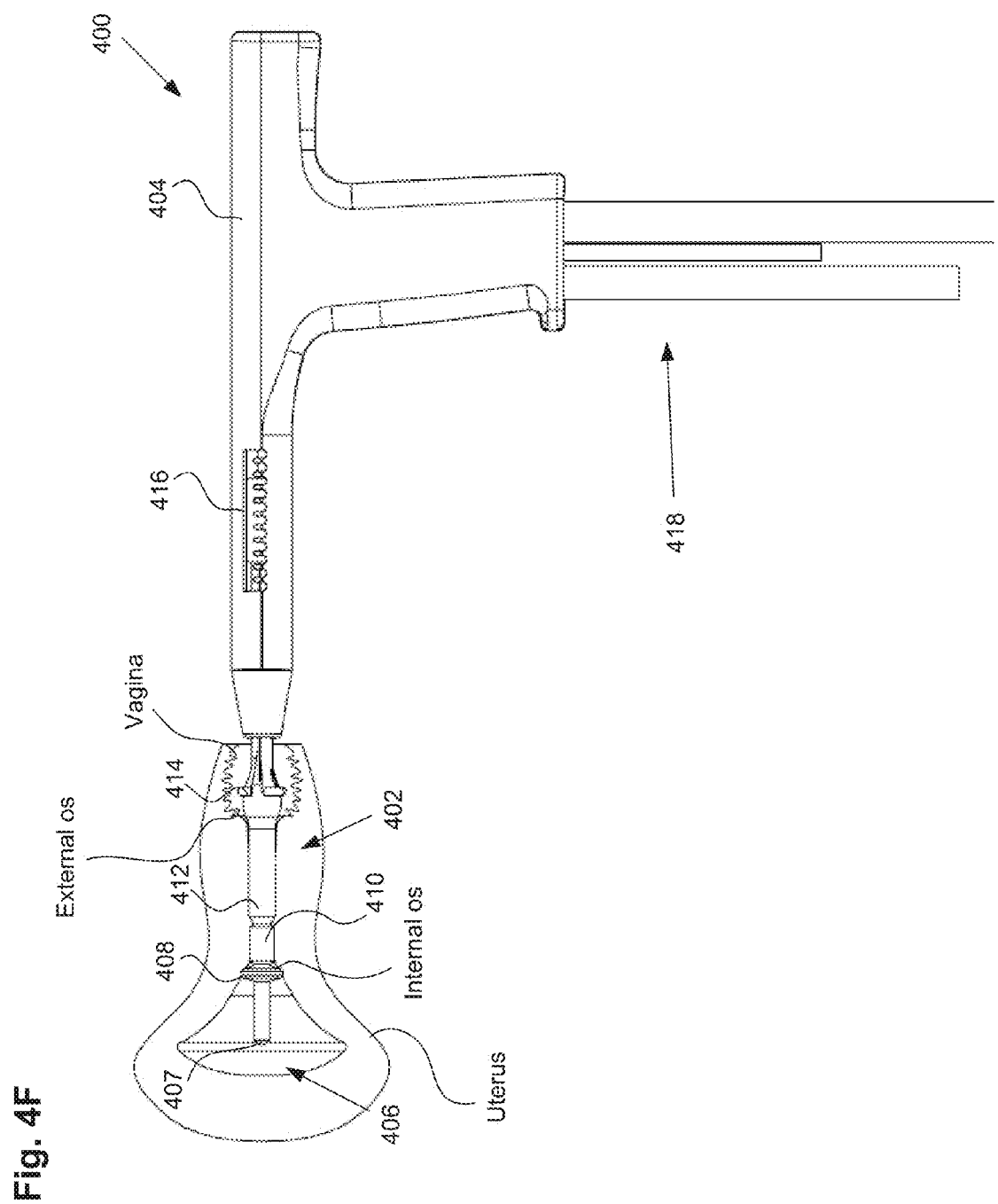

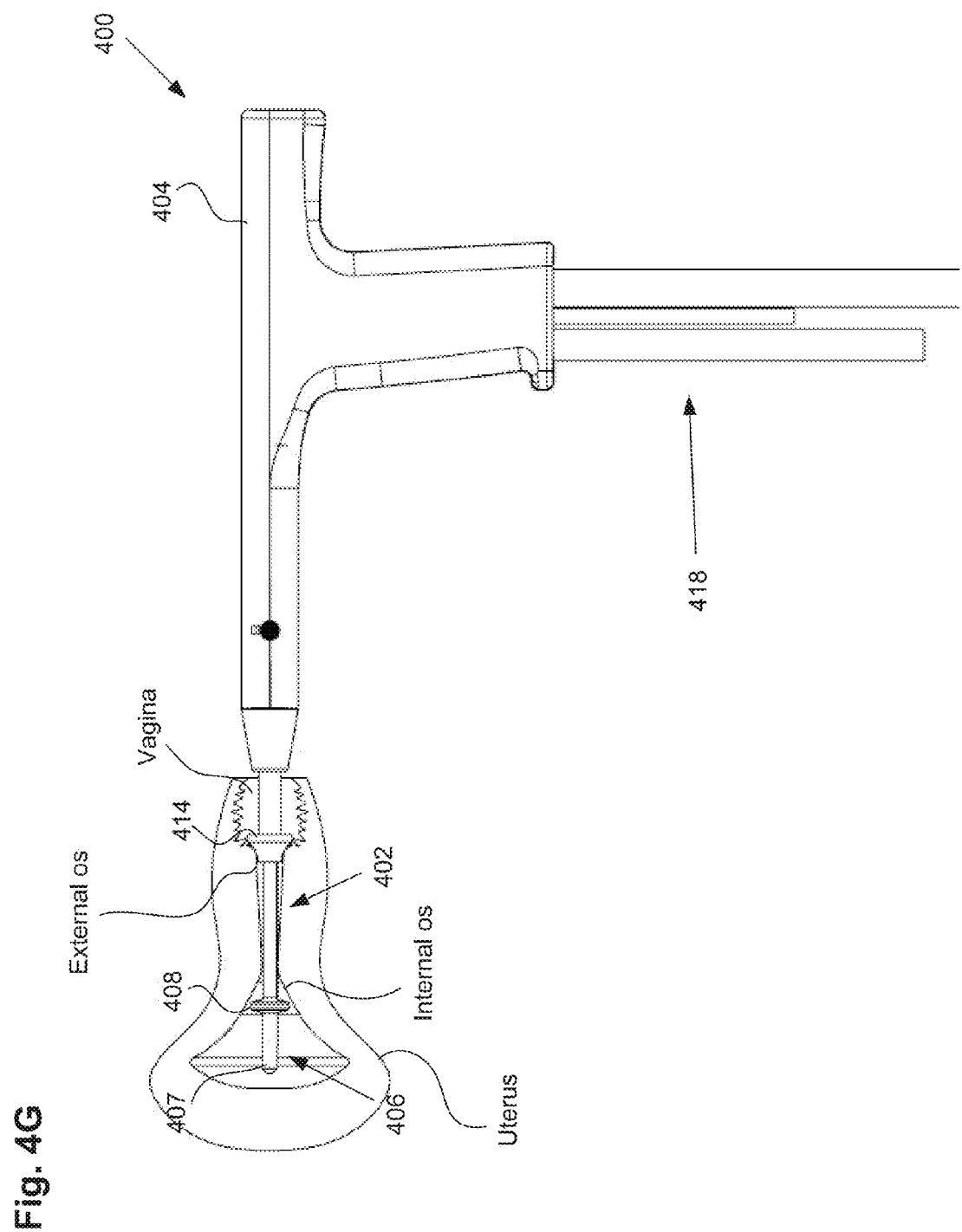

POSITIONING METHOD AND APPARATUS FOR DELIVERING VAPOR TO THE UTERUS

CROSS REFERENCE TO RELATED APPLICATIONS

This application is a continuation of U.S. patent application Ser. No. 13/292,889, filed Nov. 9, 2011, now U.S. Pat. No. 9,743,974, which application claims the benefit under 35 U.S.C. § 119 of U.S. Provisional Patent Application No. 61/411,840, filed Nov. 9, 2010, titled "Uterine Vapor Therapy Device", and U.S. Provisional Patent Application No. 61/544,885, filed Oct. 7, 2011, titled "Positioning Method And Apparatus For Delivering Vapor to the Uterus", all of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention generally relates to endometrial ablation. More specifically, the present invention relates to endometrial ablation with a heated vapor.

BACKGROUND OF THE INVENTION

Endometrial ablation (i.e., the removal or destruction of the endometrial lining of the uterus) is used as an alternative to hysterectomy for treating menorrhagia, or other uterine diseases. One prior technique for performing endometrial ablation employs a resectoscope (i.e., a hysteroscope with a built-in wire loop or other ablative devices) that is inserted transcervically into the uterus, and uses radio-frequency electrical current (RF current) to remove or coagulate the endometrial tissue. These standard techniques typically are performed in a hospital setting.

Some approaches make use of heated fluid to ablate the endometrium. For example, early journal articles describe the use of steam to treat uterine hemorrhage. See, e.g., Van de Velde, "Vapo-Cauterization of the Uterus," Amer. J. Med. Sci., vol. CXVIII (1899); Blacker, "Vaporization of the Uterus," J. Obstet. & Gyn., pp. 488-511 (c. 1901). The use of steam for this purpose was later discredited, apparently due to patient morbidity and mortality. See, e.g., Fuller U.S. Pat. No. 6,139,571. More recent descriptions of the use of injecting hot fluid into the uterus have been described. Uterine therapies employing a contained fluid have also been described.

One previous solution utilizes a balloon-based system using ultrasound as the energy source. High frequency, or radiofrequency (RF), energy has been used to perform thermal ablation of endometrial tissue. Current products for performing endometrial ablation include the NovaSure® procedure and a system marketed under the trade name THERMACHOICE®, by Ethicon, Inc. of Somerville, N.J. Cryogenic ablation, or "cryoablation," is another endometrial treatment approach.

SUMMARY OF THE DISCLOSURE

A method of delivering vapor to a uterus of a patient, comprising: inserting a portion of a uterine ablation device into the uterus of the patient; expanding a distal anchor of the uterine ablation device in the uterus; inflating a proximal balloon of the uterine ablation device to pull the uterine ablation device proximally and place the distal anchor against an internal os of the patient; inflating a central balloon within the cervical canal; and delivering a heated vapor to the uterus to ablate uterine tissue.

In some embodiments, the inserting step further comprises inserting the uterine ablation device into the uterus of the patient so as to position a distal tip of the device distally to the internal os of the patient.

In some embodiments, the expanding the distal anchor step further comprises inflating the distal anchor distally to the internal os of the patient.

In one embodiment, the distal anchor comprises a distal balloon. The distal balloon can comprise a donut shape.

In another embodiment, the distal anchor comprises a distal expandable frame.

In some embodiments, the inflating the proximal balloon step further comprises inflating the proximal balloon against a cervical canal, an external os, and a vagina of the patient.

In one embodiment, the inflating the central balloon step further comprises inflating the central balloon against a cervical canal and the internal os of the patient.

In some embodiments, the inflating the proximal balloon step is performed after the inflating the distal expansion mechanism step. In other embodiments, the central balloon step is performed after the inflating the proximal balloon step.

In one embodiment, the method comprises, prior to the delivering step, collapsing the distal anchor of the uterine ablation device.

A uterine ablation device is also provided, comprising a shaft sized and configured to access a uterus of a patient, the shaft being coupled to a vapor source, vapor delivery ports disposed on a distal portion of the shaft, a distal anchor positioned proximally on the shaft from the vapor delivery ports, a central balloon positioned proximally to the distal anchor, the central balloon configured to contact an internal os and a cervical canal of the patient when the distal anchor is positioned in the uterus against the internal os, and a proximal balloon positioned proximally to the sealing balloon, the proximal balloon configured to span from the cervical canal into a vagina of the patient when the distal anchor is positioned against the internal os.

In some embodiments, the device further comprises a filter portion disposed on the distal portion of the shaft, the filter portion configured to remove vapor from the uterus but prevent removal of tissue, blood clots, or debris from the uterus.

In some embodiments, the central balloon has a length along the shaft of approximately 15 mm to 25 mm.

In another embodiment, the distal anchor has a length along the shaft of approximately 3 mm to 10 mm.

In some embodiments, the proximal balloon has a length along the shaft of approximately 50 mm to 70 mm.

A method of delivering vapor to a uterus of a patient with a uterine ablation device is also provided, comprising inserting a distal tip of the uterine ablation device inside the uterus, positioning a distal anchor of the uterine ablation device within the uterus distally from an internal os, positioning a proximal balloon of the uterine ablation device partially within a cervical canal and partially within a vagina of the patient, positioning a central balloon of the uterine ablation device within the cervical canal, expanding the distal anchor, after expanding the distal anchor, inflating the proximal balloon to pull the distal anchor proximally against the internal os, after inflating the proximal balloon, inflating the central balloon to seal the cervical canal, and delivering a heated vapor to the uterus to ablate uterine tissue.

A uterine ablation device is provided comprising a shaft sized and configured to access a uterus of a patient, the shaft comprising a vapor delivery lumen and a vapor removal lumen, vapor delivery ports disposed on a distal portion of the shaft and coupled to the vapor delivery lumen, at least one vapor removal port disposed on the distal portion of the shaft and coupled to the vapor removal lumen, a filter disposed over the at least one vapor removal port, a distal anchor positioned proximally on the shaft from the vapor delivery ports; a central balloon positioned proximally from the distal anchor, the central balloon having a length along the shaft of approximately 15 mm to 25 mm, and a proximal balloon positioned proximally from the central balloon, the proximal balloon configured having a length along the shaft of approximately 50 mm to 70 mm.

In some embodiments, the vapor delivery lumen is disposed within the vapor removal lumen.

In another embodiment, the vapor delivery ports, the at least one vapor removal port, and the filter are disposed on a filter tip distal to the distal anchor, wherein the vapor removal port comprises at least 70% of the surface area of the distal tip.

In one embodiment, the vapor delivery ports, the at least one vapor removal port, and the filter are disposed on a filter tip distal to the distal anchor, wherein the vapor removal port comprises at least 80% of the surface area of the distal tip.

In some embodiments, the filter comprises a porosity of a 300 micron pore size with an open area of 36-50%.

A method of delivering vapor to a uterus of a patient is provided, comprising inserting a portion of a uterine ablation device into the uterus of the patient, expanding a distal anchor of the uterine ablation device in the uterus, engaging a cervical collar of the uterine ablation device against an external os of the patient to pull the uterine ablation device proximally and place the distal anchor against an internal os of the patient, inflating a central balloon within the cervical canal to seal off the cervix from the uterus, and delivering a heated vapor to the uterus to ablate uterine tissue.

In some embodiments, the engaging step further comprises engaging a spring-loaded cervical collar against the external os.

A filtering tip of a vapor ablation device is provided, comprising a vapor delivery port adapted to receive vapor from a vapor delivery lumen and deliver the vapor near a target tissue, a vapor return port adapted to remove vapor to a vapor removal lumen, a filter disposed over at least the vapor return port, the vapor return port comprising at least 70% of an external surface area of the filtering tip so as to provide a vapor removal function if a portion of the filter is obstructed.

In some embodiments, the vapor return port comprises at least 80% of the external surface area of the filtering tip.

In another embodiment, the tip is substantially flexible.

In some embodiments, the vapor delivery lumen and the vapor removal lumen are substantially flexible.

In another embodiment, the vapor removal lumen is disposed around at least a portion of the vapor delivery lumen.

In some embodiments, the filter has a pore size of approximately 250 to 350 microns with an open area of approximately 36 to 50% to allow vapor to pass but prevent blood clots, tissue, and other bodily materials from passing.

In one embodiment, the vapor delivery port is disposed near a distal portion of the filtering tip, and the vapor return port comprises substantially the remainder of the surface area of the filtering tip.

BRIEF DESCRIPTION OF THE DRAWINGS

FIGS. 1A, 1B, 1C, 1D and 1E illustrate one embodiment of a uterine ablation device.

FIGS. 3A, 3B, 3C and 3D illustrate one embodiment of a distal filter tip of a uterine ablation device.

FIGS. 4A, 4B, 4C, 4D, 4E, 4F, 4G and 4H illustrate methods of using a uterine ablation device.

DETAILED DESCRIPTION OF THE INVENTION

Figure 1B:
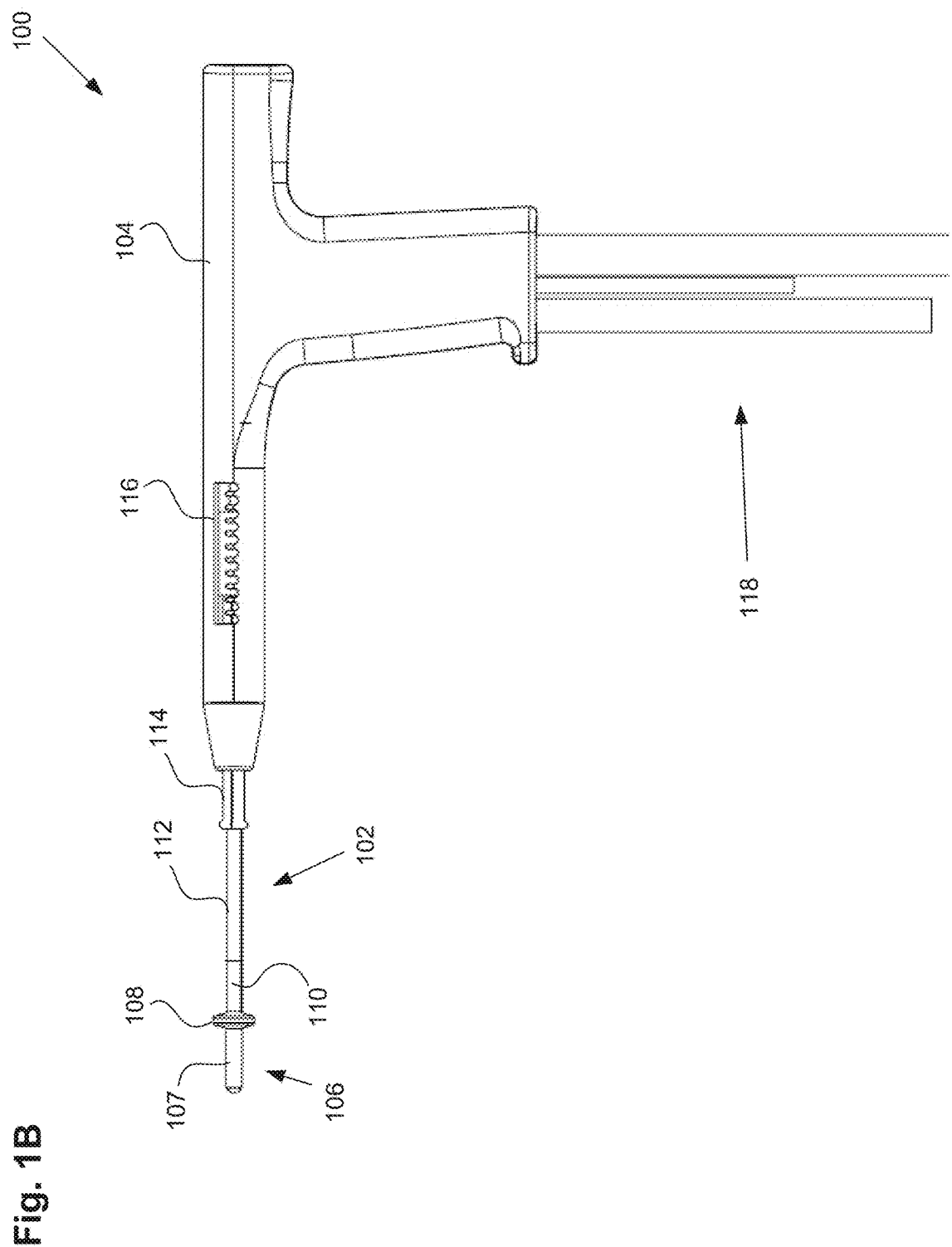

FIG. 1A illustrates a uterine ablation device 100 sized and configured to access the endometrium of a uterus and to deliver a heated vapor to the uterus to ablate uterine tissue. The device can be configured to ablate and treat the endometrial lining of the uterus as an alternative to hysterectomy for treating menorrhagia or other uterine diseases. The device 100 can include shaft 102, handle 104, distal tip 106, vapor ports 107, distal anchor or distal balloon 108, central or sealing balloon 110, proximal or positioning balloon 112, cervical collar 114, cervical measurement 116, and connection lumens 118, which can couple the uterine ablation device to a control system (not shown) comprising a computer, a vapor generation system, and mechanisms configured to inflate and deflate the balloons as well as control the delivery and removal of vapor from the device. Handle 104 can be an ergonomic handle and can include features and controls for using the device (e.g., buttons, levers, indicia for providing feedback for depths of insertion, valves, etc.), including features for controlling inflation of balloons 108, 110, and 112, and for controlling the delivery and removal of heated vapor from the device. It should be noted that in some embodiments, the distal anchor comprises a balloon, but in other embodiments, the distal anchor comprises an expandable anchor or expansion mechanism, such as expandable frames, filters, nets, or cages. For purposes of this disclosure, however, the distal anchor may be referred to as a distal anchor or as a distal balloon.

Cervical collar 114 and cervical measurement 116 can provide a mechanism for properly inserting the uterine ablation device the correct distance into the patient's uterus. The cervical collar is configured to abut an external os of the cervix to prevent advancing the device too far and puncturing the uterine wall. Since uterine ablation procedures are typically conducted without the use of video or real time imaging, the cervical collar can provide a palpable indicator of the location of the external face of the cervix to prevent damage to the uterus from over-insertion. For example, prior to a uterine ablation procedure, a physician can measure the distance from the external os of the cervix to the internal os of the uterus (e.g., the physician can measure the length of the cervix) and compare that length with the total overall length from the external os of the cervix to the interior fundus of the uterus. Next, the physician can adjust cervical measurement 116 to coincide with the measured cervical length. Adjusting cervical measurement 116 causes cervical collar 114 to slide axially along shaft 102, either lengthening or shortening the distance from distal tip 106 to the cervical collar 114. Thus, the cervical collar 114 can be adjusted based on the cervical measurement to aid in positioning the distal tip of the uterine ablation device in the proper position within the uterus (e.g., just past the internal os of the cervix, or in some embodiments, approximately 1 cm past the internal os). When the cervical collar has been properly positioned along the shaft of the device, the physician can insert the device into the patient until the cervical collar touches the external os of the cervix, thereby placing the distal tip of the device within the uterus of the patient without puncturing the distal wall of the uterus.

The cervical collar 114 can be configured as a cylindrical shape and can comprise a soft, low durometer material such as silicone that can slide along the shaft to circumferentially surround the positioning balloon 112, but can expand easily when the positioning balloon is inflated. The distal portion of the cervical collar can have a variety of shapes to provide an atraumatic, non-penetrating surface. In some embodiments, the cervical collar does not surround the entire shaft but instead has a curved/hooked shape and can be made from a material such as stainless steel, polyethylene, or biocompatible material. In other embodiments, the cervical feeler can include a T-shape, a semi-circular footing, or a rounded shape. In some embodiments, more than one cervical feeler can be used so as to provide for multiple places of contact with the external os of the patient. Also, it may be preferable for the physician to pick and identify one spot on the external cervical face to make his internal fundal and cervical length measurements. This is because the cervix may not present itself as a normal, horizontal surface. As an example, picturing the cervix as a clock face, the physician may choose a location at 3 o'clock on the cervix. It may be preferable to have the cervical feeler attached to the cylindrical marking device on a rotatable collar so that the surgeon can ensure that the feeler hits the same reference point.

The balloons described herein can be any type of flexible balloon, such as rubber, latex, urethane, silicone, PET, LDPE, parylene, nylon, PE, combinations of these polymers, or can be manufactured from any other suitable material as known in the art.

Shaft 102 can be configured to deliver a heated vapor from a remote vapor source (not shown) through the device and out of vapor ports 107 in distal tip 106. The shaft can also be configured to return vapor that has exited the device, including bodily fluids, uterine materials, and condensate back through the vapor ports and into the shaft. In FIG. 1A, vapor ports 107 can include both vapor delivery and vapor return ports. In some embodiments, vapor delivery ports are separate and distinct from the vapor return ports, and in other embodiments, the same ports are used for both vapor delivery and vapor return. The vapor delivery ports are configured to provide an even distribution of heated vapor through a cavity or a balloon, an inflatable membrane or other porous structure, and may comprise small lumens or holes on the end of the shaft. The vapor return ports, in contrast, are configured to return used vapor and condensate, and may comprise larger slots to prevent blood, tissue, etc from blocking or clogging the return lumen. In some embodiments, as will be discussed in detail below, the entire distal tip 106 of the device, including vapor delivery and vapor return ports, can be covered with a mesh so as to filter any materials that may clog or obstruct the device.

Referring still to FIG. 1A, uterine ablation device 100 is shown in a collapsed delivery configuration, with distal balloon 108, sealing balloon 110, and positioning balloon 112 deflated to reduce the cross sectional diameter of the device and can be 6 mm in diameter during insertion or smaller. When the device is in the delivery configuration, the reduced profile allows for easier access to through the vagina, cervical canal, and cervix to gain access to the uterus, and provides reduced patient discomfort during insertion. In some embodiments, the outer dimensions of the uterine ablation device are such that introduction of the device into the uterine cavity can be achieved without the need for mechanical or pharmacological dilation of the os prior to device introduction.

FIG. 1B illustrates the uterine ablation device 100 of FIG. 1A with distal balloon 108 inflated. As shown the distal balloon 108 can comprise a disk or donut-like shape, so as to extend radially outward enough to provide adequate positioning within the uterus, while remaining narrow enough so as to block a minimal amount of tissue an not interfere with the vapor therapy. In some embodiments, the distal balloon can comprise a length along shaft 102 of approximately 3 to 10 mm and can comprise a diameter of approximately 13 to 16 mm. In other embodiments, the distal balloon can comprise other shapes, including spherical, tubular, or football shaped balloons. In some embodiments, the distal balloon can be replaced with a mechanical expansion mechanism such as flanges, hinges, frames, cages, filters, or nets that can be expanded by push-pull mechanisms of the outer shaft, or rotation of the outer shaft, in relation to an inner shaft connected to the mechanical expansion mechanism.

The distal balloon 108 can be inflated with a fluid, such as saline, or alternatively, can be inflated with air or gas. The distal balloon can be inflated with a room temperature medium, a cooled medium, or alternatively, a heated medium. In one embodiment, the positioning balloon can be filled with an echogenic medium. In another embodiment, the positioning balloon can be inflated with a saline and air bubbles mixture to allow for greater echogenicity via ultrasound imaging. In some embodiments, the positioning balloon includes a conductive coating to allow for heat transfer from the heated vapor through the conductive coating to the tissue. The positioning balloon can be molded or formed with structural grooves, ridges, or indentations that allow for vapor or heated materials to flow around the positioning balloon to treat the tissue in contact and proximal to the positioning balloon. The distal balloon is configured to be positioned just distal (approximately 1 cm) from the internal cervical os. This area of treatment just distal to the internal cervical os is generally referred to as the lower uterine segment.

The distal balloon can typically be inflated to a pressure of approximately 20 to 30 psi. With the distal balloon inflated to this inflation pressure, the axial force required to pull out the device from the uterus can range from 2 to 5 lbs. of force. In some embodiments, this inflation pressure is the pressure required to prevent accidental removal of the inflated balloon from the uterus, through the cervix.

FIGS. 1C-1D illustrate the uterine ablation device 100 of FIGS. 1A-1B with the positioning or proximal balloon 112 also inflated. As shown in FIGS. 1C-1D, both the distal balloon 108 and the positioning balloon 112 are inflated. The positioning balloon can also be inflated with a fluid, such as saline, or alternatively, can be inflated with air. In some embodiments, the proximal balloon can comprise a length along shaft 102 of approximately 50 mm to 70 mm. In another embodiment, the proximal balloon comprises a length along the shaft of approximately 40 mm to 90 mm. The length of the proximal balloon, and its distance along the shaft from distal balloon 108, ensures that when inflated, the proximal balloon will span the patient anatomy from at least a portion of the cervix, past the external os, and into the vagina. The proximal balloon can be inflated with a room temperature medium, a cooled medium, or alternatively, a heated medium. In FIG. 1C, the positioning balloon 112 is inflated, but the cervical collar 114 is positioned proximally from the positioning balloon so that inflation of the balloon does not expand the collar. In FIG. 1D, however, the cervical collar 114 is advanced distally along shaft 102 so as to partially surround positioning balloon 112. In this embodiment, when the proximal balloon is expanded, the cervical collar 114 is configured to expand radially outwards with the balloon, as shown.

Figure 1E:
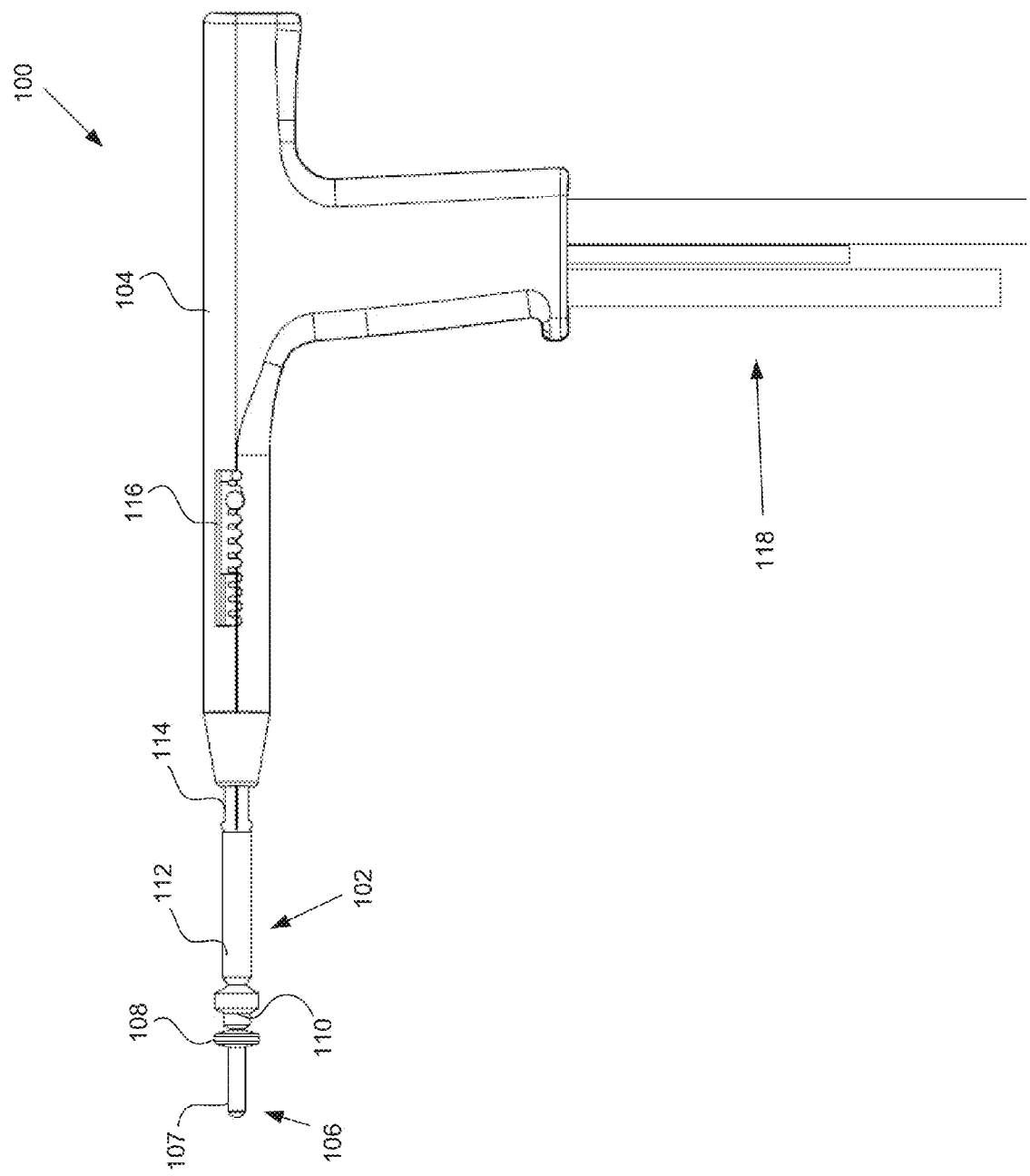

FIG. 1E illustrates the uterine ablation device 100 of FIGS. 1A-1D with all three balloons inflated, including distal balloon 108, central sealing balloon 110, and positioning balloon 112. The central balloon can be inflated with a fluid, such as saline, or alternatively, can be inflated with air. The positioning balloon can be inflated with a room temperature medium, a cooled medium, or alternatively, a heated medium. In some embodiments, the central sealing balloon comprises a length along shaft 102 of approximately 15 mm to 25 mm. The central balloon can be disposed on the shaft between the distal balloon or anchor and the proximal balloon. In some embodiments, the central balloon is adjacent to both the distal balloon and the proximal balloon. In other embodiments, there is a small gap or space between one or more of the balloons. The length and position of the central balloon on the shaft ensures that when inflated, the central balloon seals the cervix off from the uterus near the internal os, but the balloon does not extend into the uterus or into the vagina of the patient. The central and proximal balloons can comprise any diameter, but preferably should have a diameter large enough to be able to engage the walls of the cervix and/or the vagina in the average female patient.

Figure 2:
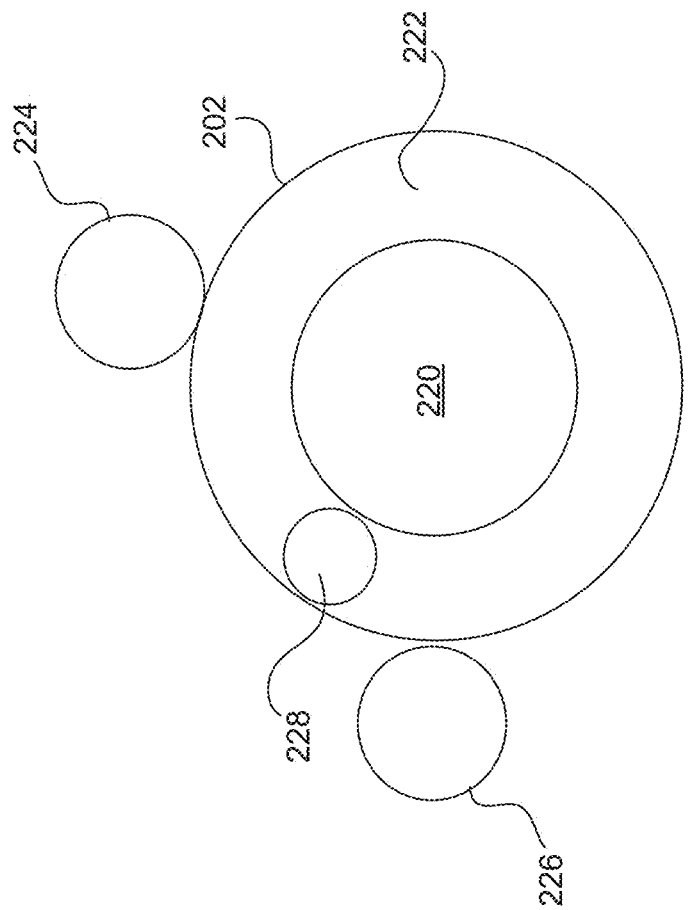
FIG. 2 illustrates a cross sectional view of a shaft of a uterine ablation device.

FIG. 2 illustrates a cross sectional view of shaft 202, which can correspond with shaft 102 of FIGS. 1A-1E above. The shaft can include vapor delivery lumen 220, vapor return lumen 222, and balloon inflation lumens 224, 226, and 228 corresponding to each of the distal balloon, sealing balloon, and positioning balloon described above.

Vapor delivery lumen 220 can be a central lumen within shaft 202 configured to deliver a heated high-quality vapor through the uterine ablation device to tissue. The vapor delivery lumen can be coupled to a vapor source, and can transport vapor from the vapor source to the distal tip of the device and out towards tissue via vapor delivery ports. The vapor delivery lumen can be concentrically placed within vapor return lumen 222, as shown. In some embodiments, the positions of vapor delivery lumen and vapor return lumen can be switched. Balloon inflation lumens 224, 226, and 228 can be configured to inflate and deflate the three balloons described above. It should be understood that the individual inflation lumens can be used for other balloons and other devices in additional embodiments. In some embodiments, one or more balloon inflation lumens are positioned external to shaft 202, and in other embodiments, one or more balloon inflation lumens are positioned within shaft 202, such as within vapor return lumen 222 as shown in FIG. 2. In one embodiment, a sensor (such as a fiber optic sensor) or thermocouple lead can be placed through an inflation lumen along the length of the shaft so as to position the sensor on or near the distal tip of the device.

In additional embodiments, lumens 220 and 222 can be off-center, or alternatively, the lumens need not be concentric and can be disposed side by side. In some embodiments, the shaft 202 can be surrounded by an additional lumen containing insulation to prevent damage to tissue that comes into contact with the shaft during vapor delivery. The shaft can be made from a variety of rigid and flexible materials such as stainless steel, titanium, Nitinol®, PEEK, polycarbonate, PET, and polyimide. In some embodiments the shaft may comprise multi-lumen extrusions for ease of assembly.

FIGS. 3A-3D illustrate one embodiment of a distal tip 306, corresponding to distal tip 106 of FIGS. 1A-1E. FIG. 3A illustrates a side view of distal tip 306, including a filter or mesh 330 configured to keep blood and tissue out of the return lumen of the shaft. The mesh 330 can cover the vapor ports, vapor return ports, vapor delivery lumen, and vapor return lumen, but still allow for the delivery and return of vapor to a patient. Additionally, the mesh structure can help protect and maintain in position internal components such as the vapor delivery elements and measurement devices such as pressure and temperature sensors within the tip. In some embodiments, the mesh can be made from a fluoropolymer, PET, nylon, or PE material. In a further refinement, the mesh can be provided with a certain porosity and geometry to create filter made from PET with about a 300 micron pore size (with an open area of 36-50%) to create an optimum flow through for vapor return with the ability to reduce the amount of particulates and other bodily materials from entering the return lumen. In some embodiments, the distal tip is rigid, and in other embodiments the tip incorporates flexibility so that it conforms to the anatomy of the uterine cavity to prevent damage or perforation of the uterine wall, while maintaining column strength sufficient to allow easy introduction through the os, into the uterine cavity. In another embodiment, the filter can be made to expand in the uterine cavity to increase the amount of surface area available for filtering material from the uterine cavity. This expansion can be created be mechanically advancing the distal end of the filter tip, rotating the outer shaft and unrolling the distal filter tip, or expanding and stretching corrugations in the filter tip.

FIG. 3B is a cross sectional view of the distal tip of FIG. 3A, showing the internal elements of the distal tip. As shown, the distal tip can incorporate supportive elements 332, such as coils or ribbons, to maintain its cylindrical shape and support the mesh in place. As shown in the cross sectional view, vapor delivery lumen 320 can be positioned centrally to the distal tip, and surrounded by supportive elements 332 and mesh 330. The vapor delivery lumen 320 can terminate at vapor ports 307, which are configured to spray or deliver vapor from the distal tip of the device. The remaining volume within the distal tip can comprise vapor return lumen 322, which, as described above, can be a concentric lumen to vapor delivery lumen 320. Maximizing the surface area available for the vapor return lumen can prevent clogging during operation of the device. Thus, in some embodiments, the vapor delivery ports can comprise as little as 10% of the surface area of the distal tip, and the vapor return ports or vapor return lumen can comprise as much as 80% of the surface area of the distal tip and in some embodiments higher surface areas of up to approximately 95%.

In some embodiments, the distal tip contains nozzles for delivering the vapor in a spray pattern. The plurality of nozzles or ports can help prevent obstruction of the vapor source by the surrounding tissue, such as in cases where the device embeds partially into the uterine wall. In some embodiments, separate vapor ports are coupled to the delivery and return lumens. The vapor delivery ports can comprise slits, holes (as shown in FIG. 3B), or various other nozzle shapes configured to deliver a heated vapor from the ablation device.

FIGS. 3C and 3D illustrate one embodiment of a split chamber tip 334 having vapor delivery ports 307 that can be used at the distal end of distal tip 306. Slot 336 can be configured to receive the vapor delivery lumen described above. As shown in the cross-sectional view in FIG. 3D, the split chamber tip 334 can include a chamber 338 within the tip to aid in dispersing the vapor prior to reaching vapor delivery ports 307. The split chamber tip can be constructed from a porous mesh made from PET or other polymer, metallic screen, or fibers to prevent debris from entering the vapor probe.

In another embodiment, the distal tip of the device can reside within an inflatable balloon or membrane that is affixed to the shaft. Vapor that exits the distal tip can inflate the balloon that contacts the inner lining of the body cavity or uterus. The vapor ports in conjunction with the return lumen provide a continuous flow of heated vapor to the balloon or membrane while condensate and excess pressure is relieved through the distal tip and return lumen. In addition, heated vapor can be supplied preferentially and separately to the distal balloon to provide a specific heating regime to the lower uterine area near the internal os.

Compartmentally, different heating protocols can be configured with multiple balloon configurations within the bodily cavity depending upon the application, tissue mass, and the desire to minimize or maximize the amount of ablation within a certain target area of the body. As an example, separate balloon compartments can be configure to preferentially inflate in the corneal areas of the uterus where the amount of thermal energy required would be less than required in the corpus or fundus of the uterus. Conversely, different balloons or membranes can be filled with cooling media (fluid or gas) that serves to preserve that area of tissue from thermal injury. As an example, the sealing balloon and proximal positioning balloon (from the above figures) can be supplied with cooling media to protect the cervical area while the uterine cavity balloon is filled with vapor and distal balloon supplied with less vapor or intermittent vapor to reduce the amount of the thermal energy supplied in this area of the body.

Figure 4A:
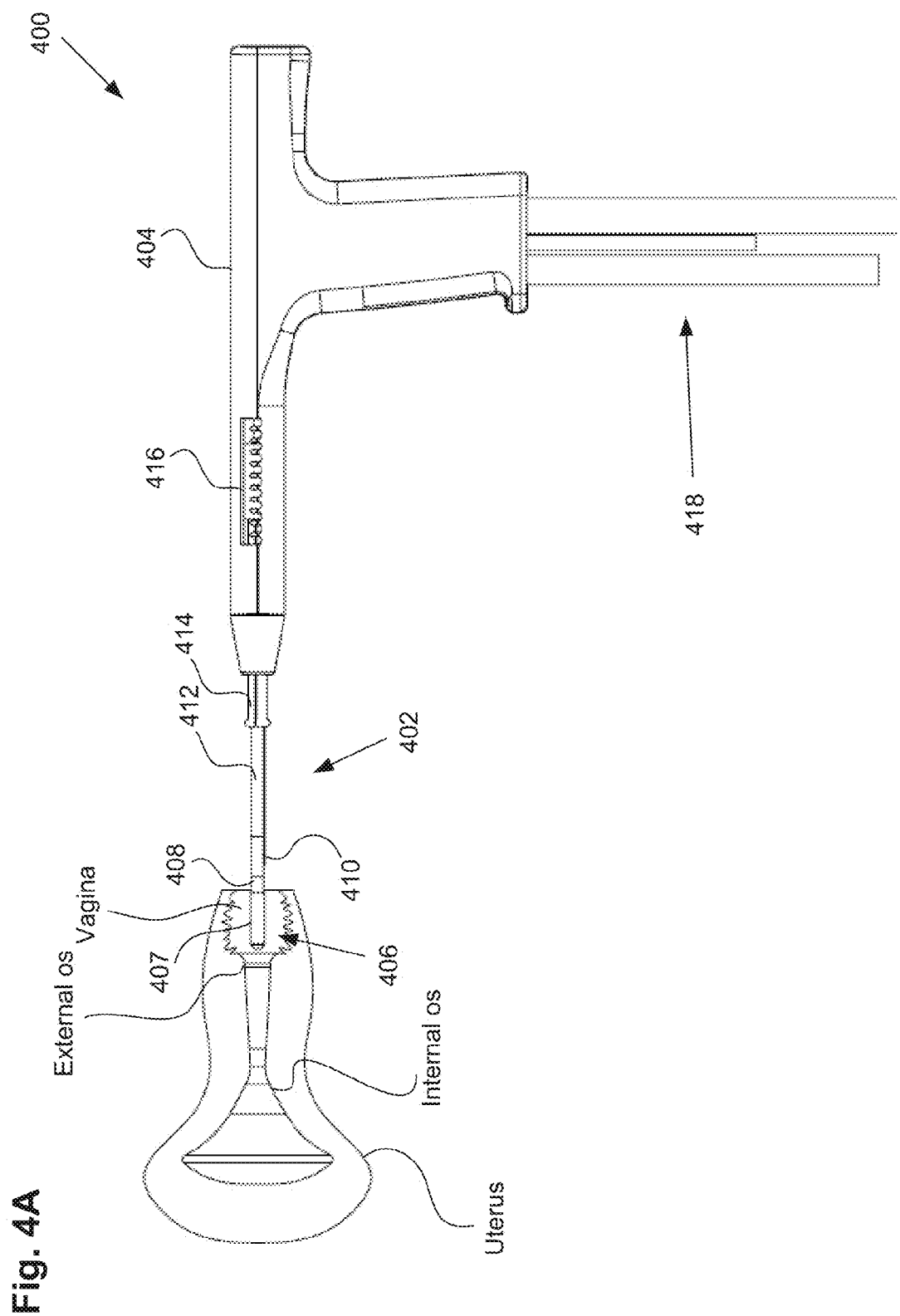

A method of using the uterine ablation device will now be described with respect to FIGS. 4A-4C. Uterine ablation device 400 of FIGS. 4A-4C can be the uterine ablation device described above. Prior to using the device, a physician can measure the length of the patient's cervix, or a distance from a reference point in the vagina to the fundus, and adjust cervical measurement 416 on device 400 to correspond to the measured or estimated cervical length. This, in turn, adjusts the position of cervical collar 414 along shaft 402 to prevent over advancement the ablation device and perforating the uterus. Referring to FIG. 4A, uterine ablation device 200 can be arranged in a delivery configuration with all three balloons 408, 410, and 412 deflated and inserted into the vagina approaching the external os of the cervix.

Next, referring to FIG. 4B, the distal tip 406 of the ablation device can be inserted past the external os into the cervical canal, and past the internal os of the patient to gain access to the uterus. In one embodiment, the distal balloon 408 is positioned within the uterus distal to the internal os, the sealing balloon 410 is positioned at or proximal to the internal os and extending into the cervical canal, and the positioning balloon 412 is positioned within the cervical canal and extending proximally into or towards the vagina. In some embodiments, as shown in FIG. 4B, cervical collar 414 abuts the external os of the cervix, preventing further advancement of the device and preventing perforation of the uterine cavity. Adjusting the distance of the cervical collar to the distal tip based on a cervical measurement can ensure proper positioning of the distal tip of the device within the uterus, such as approximately 1 cm distal to the internal os.

Referring now to FIG. 4C, once distal tip 406 of the ablation device is disposed within the uterus, just distal to the internal os, the distal balloon 408 can be inflated to the desired pressure. In some embodiments, the balloon can be inflated to a pressure of up to approximately 20 to 30 psi so as to prevent accidental withdrawal of the ablation device from the uterus. It should be noted that at this point in the method, the distal balloon is positioned slightly past the internal os of the cervix. Inflation of the distal balloon can later serve as an anchor to prevent the device from sliding proximally out of the uterus.

Figure 4D:
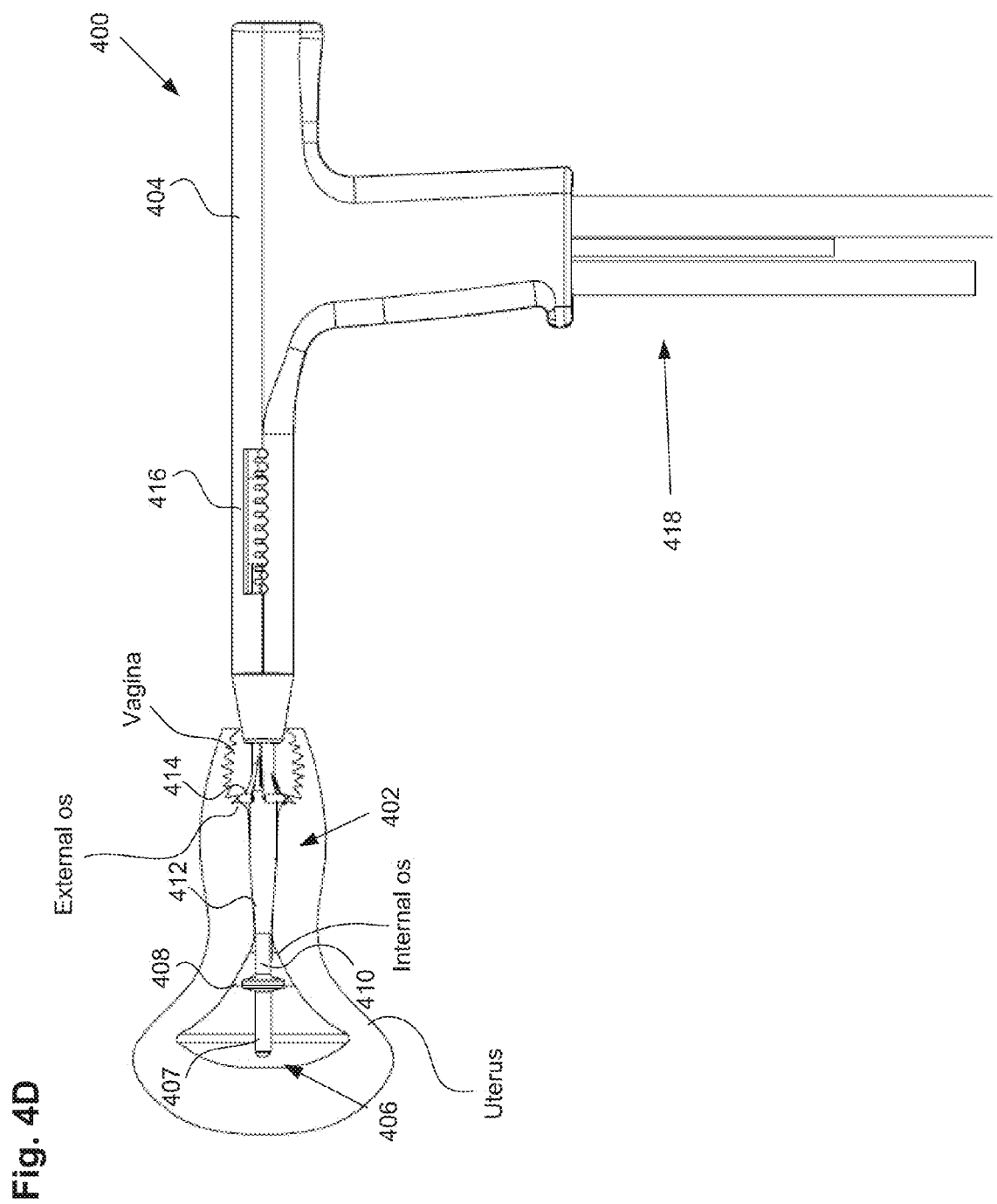
Figure 4E:
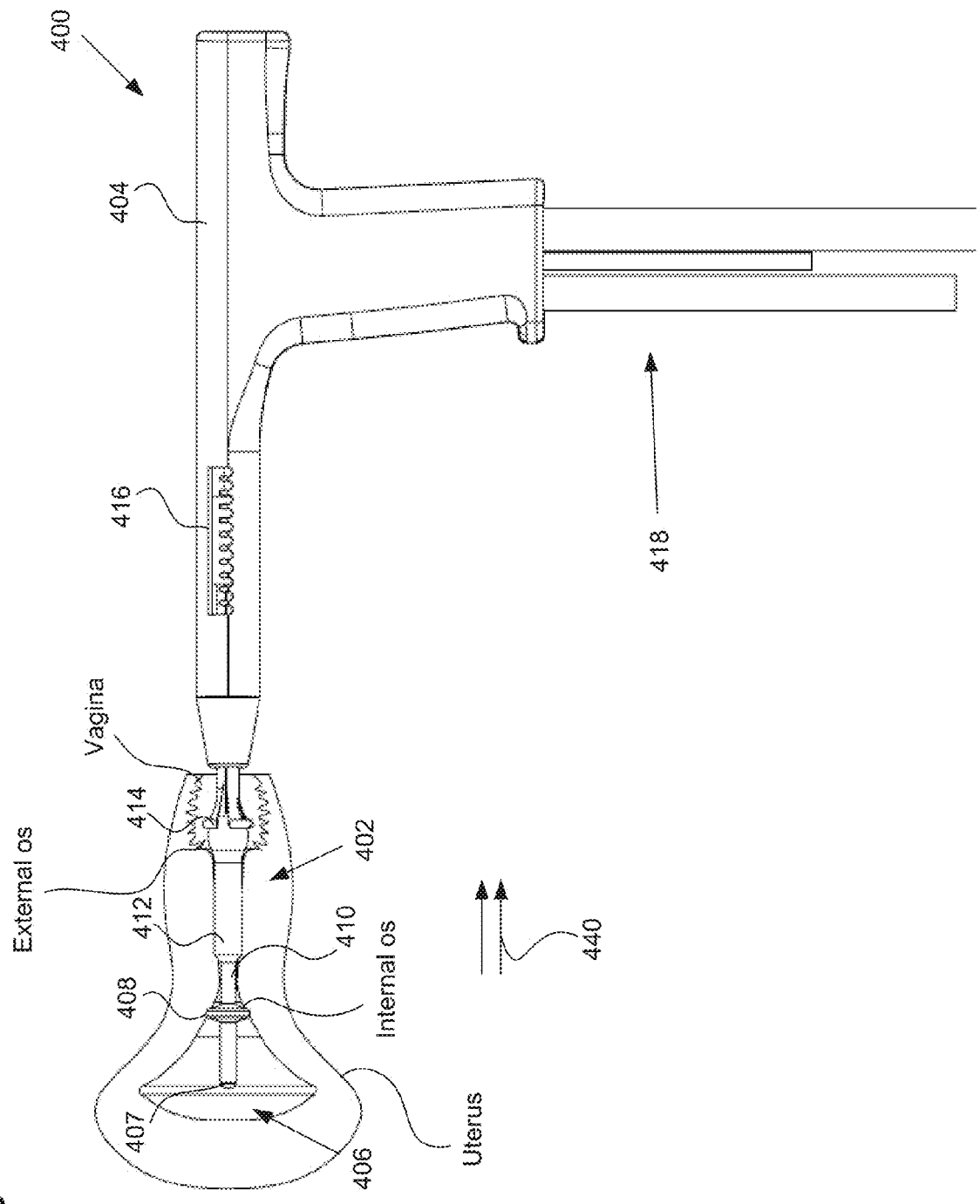

Referring now to FIG. 4D, after inflating the distal balloon, proximal balloon 412 can be inflated to cause the device to assume the positioned configuration, as shown in FIG. 4E, with the distal balloon 408 full seated against the internal os and the positioning or proximal balloon 412 expanded within the cervix and extending past the external os into the vagina. It should be noted that in FIG. 4D, the proximal balloon is only partially inflated, and the distal balloon is still a short distance away from the internal os of the cervix. As the proximal balloon is inflated, the balloon can expand outwardly from the cervix into the relatively unconstrained space of the vagina, which creates a compression force that pulls the device and distal balloon 408 proximally to engage against the interior portion of the internal os (also known as the cervical ostium or cervical os). It should also be noted that in FIG. 4D, as the proximal positioning balloon 412 expands, the cervical collar 414 is adapted to expand radially to allow expansion of the balloon, while maintaining contact with the cervix to prevent over insertion.

FIG. 4E illustrates the distal balloon fully seated against the internal os, and shows positioning balloon fully inflated and spanning the distance from a portion of the cervix to a portion of the vagina. Inflation of the positioning balloon from within the cervix out into the vagina is critical for positioning the uterine ablation device properly within the patient. As the balloon expands outwards into the vagina, it can assume a "wedge" shape, which causes the proximal device movement indicated by arrows 440 to seat the distal balloon against the internal os. The distal balloon can have a sealing effect against the internal os as the positioning balloon pulls it proximally. One advantage of the proximal positioning balloon is to standardize the amount of compression forces from patient to patient and physician to physician. In some embodiments, the compression forces range from 0.5 to 3 lbs. This consistency can ensure that a minimum amount of compression is applied for each procedure, and can eliminate the risk of one physician pulling too hard and extracting the device from the patient when the distal balloon is inflated. In one embodiment, the positioning balloon is inflated as high as 10 psi to position the device to pull the device proximally and seat the distal balloon against the internal os.

Referring now to FIG. 4F, when the ablation device, more specifically the distal balloon, is positioned against the cervical os as in FIG. 4E, sealing balloon 410 can be inflated to seal the cervical canal off from the uterus. The sealing balloon 410 is configured to seal off the uterus from the cervical canal and vagina, such as proximally to the internal os, so as to prevent leakage of vapor back into those sensitive portions of the patient's anatomy. In this figure, the sealing balloon is shown as cylindrically-shaped, but it may be advantageous to have the sealing balloon with variable geometry (e.g., with radial projections, pear-shape, bulbous proximal end) to more firmly engage the cervical canal or external os of the cervix. In one embodiment, the sealing balloon is inflated as high as 7 psi to seal off the uterus from the rest of the anatomy. The system described herein can provide for triple-redundant sealing; the distal balloon 408 against the interior surface of the internal os, the sealing balloon 410 against the interior surface of the interior os as well as along a portion of the interior surface of the cervical canal, and the positioning balloon 412 against a portion of the interior surface of the cervical canal, the exterior os, and a portion of the vagina. This arrangement provides for maximum safety for the patient as well as increased accuracy in positioning the device prior to vapor delivery and ablation.

Figure 4H:
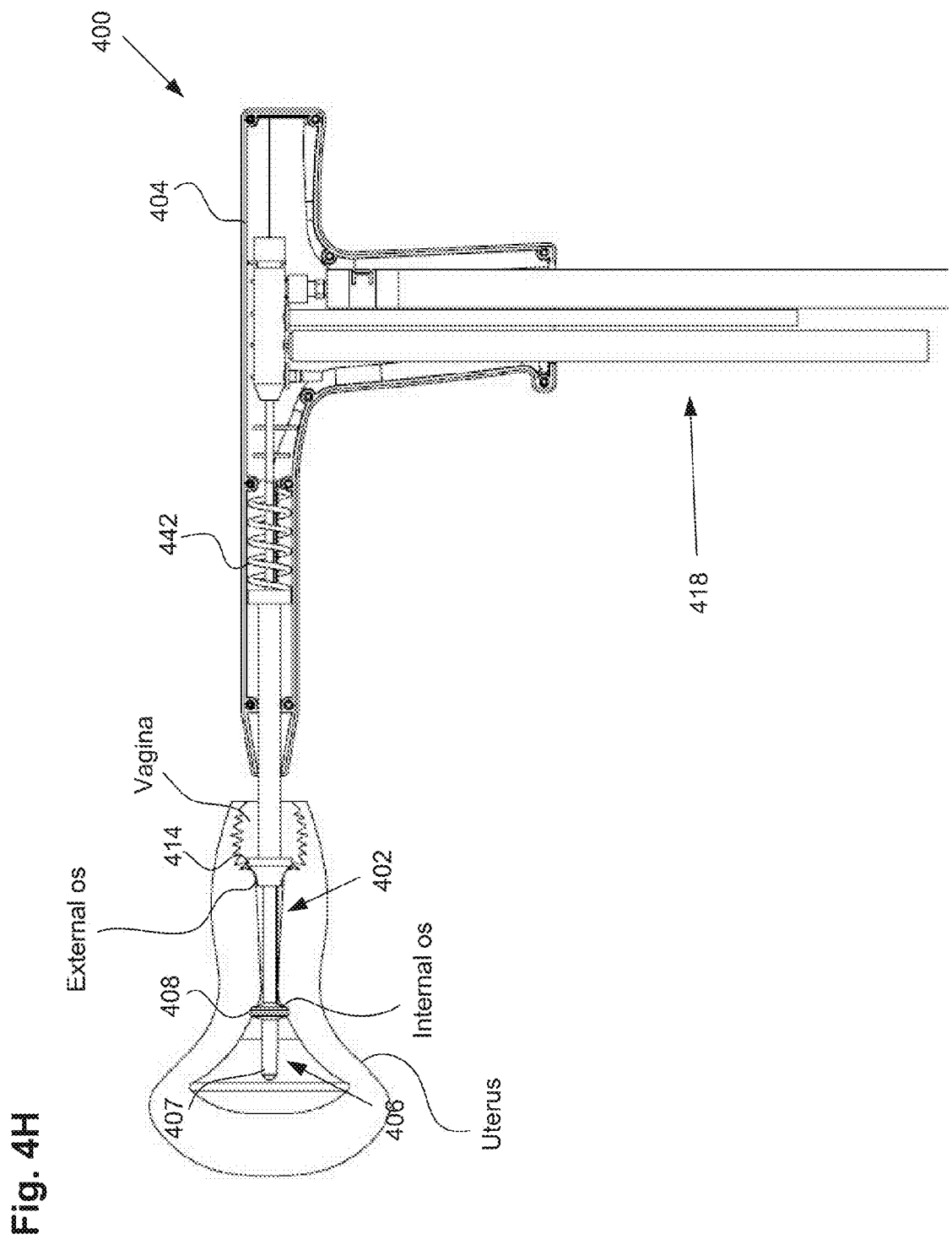

In another embodiment, referring now to FIGS. 4G-4H, the proximal balloon function can also be accomplished by a non-expandable cervical collar that is spring loaded. For example, in FIG. 4G, the distal tip of the ablation device can be positioned within the uterus, and the distal balloon or anchor 408 can be inflated or expanded distally to the internal os, as described above, and the cervical collar 414 can be placed in contact with the external os. As shown, the cervical collar in this embodiment can include a non-expandable, wedge shaped collar. In other embodiments, the cervical collar can be expandable. However, the collar should be sized and shaped so as to engage the external os and prevent the cervical collar from fully entering the cervix. Referring to FIG. 4H, the device can include a spring 442 or other force mechanism (e.g., a mechanical ratchet, a piston, a motor, etc) configured to apply force to the cervical collar. The spring can be locked into position until released, so as to allow for proper positioning of the device within the uterus. Unlocking the spring can then apply compression force or pressure on the exo cervix or external os with the cervical collar, thus pulling on the device proximally to seat the distal anchor as shown in FIG. 4H.

Once the device has been properly positioned, a heated vapor can be delivered from the distal tip 406 of ablation device 400 through vapor ports 407 into the uterus to ablate the uterine tissue. The vapor condenses on tissue and comes into direct contact with the tissue within the uterus. In some embodiments, the shaft of the uterine ablation device can include a thermocouple or other temperature sensor positioned proximally of the positioning balloon or sealing balloon to sense and indicate a vapor leak from the uterus into the cervical canal. In one embodiment, the ablation incorporates a pressure sensor in the uterine cavity. Upon completion of the ablation therapy or when a predetermined pressure has been achieved, the vapor can be removed from the uterus through the distal tip of the device. In one embodiment, the distal balloon 408 can be deflated immediately prior to, or during vapor delivery, so as to allow vapor to permeate and ablate the tissue that was formerly blocked by the distal balloon. This step is permissible and safe for the patient since sealing balloon 410 and positioning balloon 412 still provide dual redundancy for preventing vapor to escape back into the sensitive portions of the anatomy, such as the cervix and vagina.

In another method, the uterine ablation device can be positioned and used for treatment with only the distal anchor and central sealing balloon. In this embodiment, the uterine ablation device can be arranged in a delivery configuration and inserted through the vagina, cervical canal, and cervix of a patient to gain access to the uterus. Once the distal tip of the ablation device is disposed within the uterus, the distal anchor can be inflated or expanded. Upon inflating or expanding the distal balloon, the uterine ablation device can be pulled proximally (e.g., by a physician) to engage the interior portion of the cervix, the cervical ostium or internal os. When the ablation device is positioned against the internal os, the central sealing balloon can be inflated to seal the cervical canal from the uterus. Next, a heated vapor can be delivered from the ablation device through the vapor delivery ports to the uterus to ablate the uterine tissue. Upon completion of the ablation therapy or when a predetermined pressure has been achieved, the vapor can be removed from the uterus through the vapor return ports.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A uterine device, comprising:
    a shaft sized and configured to access a uterus of a patient, the shaft being coupled to a fluid source;
    fluid delivery ports disposed on a distal portion of the shaft;
    a distal balloon positioned proximally on the shaft from the fluid delivery ports;
    a central balloon positioned proximally to the distal balloon, the central balloon configured to contact an internal os and a cervical canal of the patient when the distal balloon is positioned in the uterus against the internal os;
    a proximal balloon positioned proximally to the central balloon, the proximal balloon configured to span from the cervical canal into a vagina of the patient when the distal balloon is positioned against the internal os; and
    a controller disposed within the handle and operably coupled to the distal balloon, the central balloon, and the proximal balloon, the controller configured to inflate the proximal balloon after inflating the distal balloon to create a compression force that pulls the uterine device and the distal balloon proximally to engage against an interior portion of an internal os of the patient.

2. The uterine device of claim 1 further comprising a filter portion disposed on the distal portion of the shaft, the filter portion configured to remove fluid from the uterus but prevent removal of tissue, blood clots, or debris from the uterus.

3. The uterine device of claim 1 wherein the central balloon has a length along the shaft of approximately 15 mm to 25 mm.

4. The uterine device of claim 1 wherein the distal balloon has a length along the shaft of approximately 3 mm to 10 mm.

5. The uterine device of claim 1 wherein the proximal balloon has a length along the shaft of approximately 50 mm to 70 mm.

* * * * *